US007695481B2

(12) United States Patent
Wang et al.

(10) Patent No.: US 7,695,481 B2
(45) Date of Patent: Apr. 13, 2010

(54) MEDICAL ROBOTIC SYSTEM WITH DIFFERENT SCALING FACTORS

(75) Inventors: Yulun Wang, Goleta, CA (US); Darrin Uecker, Santa Barbara, CA (US); Keith P. Laby, Santa Barbara, CA (US); Jeff D. Wilson, Santa Barbara, CA (US); Charles S. Jordan, Santa Barabara, CA (US); James W. Wright, Santa Barbara, CA (US); Modjtaba Ghodoussi, Santa Barbara, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 738 days.

(21) Appl. No.: 11/487,943

(22) Filed: Jul. 17, 2006

(65) Prior Publication Data
US 2008/0215065 A1    Sep. 4, 2008

Related U.S. Application Data

(63) Continuation of application No. 10/737,195, filed on Dec. 15, 2003, now Pat. No. 7,083,571, which is a continuation of application No. 09/557,950, filed on Apr. 24, 2000, now Pat. No. 6,699,177, which is a continuation of application No. 08/873,190, filed on Jun. 11, 1997, now Pat. No. 6,102,177, which is a continuation-in-part of application No. 08/814,811, filed on Mar. 10, 1997, now abandoned, and a continuation-in-part of application No. 08/755,063, filed on Nov. 22, 1996, now Pat. No. 5,855,583, which is a continuation-in-part of application No. 08/603,543, filed on Feb. 20, 1996, now Pat. No. 5,762,458.

(51) Int. Cl.
*A61B 19/00* (2006.01)

(52) U.S. Cl. .................. 606/130; 414/2; 901/8

(58) Field of Classification Search ................. 606/130; 414/1, 2; 901/1, 8, 41, 48; 318/568.11, 568.22
See application file for complete search history.

(56) References Cited

U.S. PATENT DOCUMENTS 977,825 A    12/1910   Murphy (Continued)

FOREIGN PATENT DOCUMENTS

DE    92 04 118.3    7/1992
EP    A-0494343      8/1985

(Continued)

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner*—John P Leubecker

(57) ABSTRACT

A system for performing minimally invasive cardiac procedures includes a pair of surgical instruments coupled to a pair of robotic arms with end effectors that can be manipulated to hold and suture tissue. The robotic arms are coupled to a pair of master handles by a controller to produce a corresponding movement of the end effectors. The movement of the handles is scaled such that the end effectors movement corresponds differently, typically smaller, than the movement performed by the hands of the surgeon. The input button allows the surgeon to adjust the position of the handles without moving the end effector, so that the handles can be moved to a more comfortable position. The system may include a robotically controlled endoscope allowing the surgeon to remotely view a surgical site. The surgeon may manipulate handles and move end effectors to perform a cardiac procedure.

17 Claims, 21 Drawing Sheets

U.S. PATENT DOCUMENTS

| | | |
|---|---|---|
| 3,171,549 A | 3/1965 | Orloff |
| 3,280,991 A | 10/1966 | Malton et al. |
| 4,058,001 A | 11/1977 | Waxman |
| 4,128,880 A | 12/1978 | Cray, Jr. |
| 4,221,997 A | 9/1980 | Flemming |
| 4,401,852 A | 8/1983 | Noso et al. |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |
| 4,503,854 A | 3/1985 | Jako |
| 4,517,963 A | 5/1985 | Michel |
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,641,292 A | 2/1987 | Tunnell et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,762,455 A | 8/1988 | Coughlan et al. |
| 4,791,934 A | 12/1988 | Brunnett |
| 4,791,940 A | 12/1988 | Hirschfeld et al. |
| 4,794,912 A | 1/1989 | Lia |
| 4,815,006 A | 3/1989 | Andersson et al. |
| 4,815,450 A | 3/1989 | Patel |
| 4,837,734 A * | 6/1989 | Ichikawa et al. ............ 700/249 |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,945,479 A | 7/1990 | Rusterholz et al. |
| 4,949,717 A | 8/1990 | Shaw |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,053,975 A * | 10/1991 | Tsuchihashi et al. ........ 700/264 |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,123,095 A | 6/1992 | Papadopulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,623 A | 7/1993 | Guthrie et al. |
| 5,236,432 A | 8/1993 | Matsen, III et al. |
| 5,251,127 A | 10/1993 | Raab |
| 5,257,999 A | 11/1993 | Slanetz, Jr. |
| 5,271,384 A | 12/1993 | McEwen et al. |
| 5,279,309 A | 1/1994 | Taylor et al. |
| 5,282,806 A | 2/1994 | Haber |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,368,015 A | 11/1994 | Wilk |
| 5,368,428 A | 11/1994 | Hussey et al. |
| 5,371,536 A | 12/1994 | Yamaguchi |
| 5,388,987 A | 2/1995 | Badoz et al. |
| 5,395,369 A | 3/1995 | McBrayer et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,442,728 A | 8/1995 | Kaufman et al. |
| 5,445,166 A | 8/1995 | Taylor |
| 5,451,924 A | 9/1995 | Massimino et al. |
| 5,455,766 A | 10/1995 | Scheller et al. |
| 5,458,547 A | 10/1995 | Teraoka et al. |
| 5,476,010 A | 12/1995 | Fleming et al. |
| 5,490,117 A | 2/1996 | Oda et al. |
| 5,506,912 A | 4/1996 | Nagasaki et al. |
| 5,512,919 A | 4/1996 | Araki |
| 5,544,654 A | 8/1996 | Murphy et al. |
| 5,562,503 A | 10/1996 | Ellman et al. |
| 5,571,110 A | 11/1996 | Matsen, III et al. |
| 5,572,999 A * | 11/1996 | Funda et al. ................. 600/118 |
| 5,609,560 A | 3/1997 | Ichikawa et al. |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A | 12/1997 | Taylor et al. |
| 5,696,574 A | 12/1997 | Schwaegerle |
| 5,696,837 A | 12/1997 | Green |
| 5,718,038 A | 2/1998 | Takiar et al. |
| 5,737,711 A | 4/1998 | Abe |
| 5,749,362 A | 5/1998 | Funda et al. |
| 5,754,741 A | 5/1998 | Wang et al. |
| 5,766,126 A | 6/1998 | Anderson |
| 5,779,623 A | 7/1998 | Bonnell |
| 5,784,542 A * | 7/1998 | Ohm et al. .................. 700/260 |
| 5,800,423 A | 9/1998 | Jensen |
| 5,807,284 A | 9/1998 | Foxlin |

| | | | |
|---|---|---|---|
| 5,807,379 A | 9/1998 | Jensen et al. | |
| 5,808,665 A | 9/1998 | Green | |
| 5,810,880 A | 9/1998 | Jensen et al. | |
| 5,813,813 A | 9/1998 | Daum et al. | |
| 5,814,038 A | 9/1998 | Jensen et al. | |
| 5,817,084 A | 10/1998 | Jensen | |
| 5,825,862 A | 10/1998 | Wright et al. | |
| 5,828,813 A * | 10/1998 | Ohm | 700/260 |
| 5,836,869 A | 11/1998 | Kudo et al. | |
| 5,844,824 A | 12/1998 | Newman et al. | |
| 5,855,583 A | 1/1999 | Wang et al. | |
| 5,859,934 A | 1/1999 | Green | |
| 5,860,995 A | 1/1999 | Berkelaar | |
| 5,867,210 A * | 2/1999 | Rod | 348/51 |
| 5,876,325 A | 3/1999 | Mizuno et al. | |
| 5,878,193 A | 3/1999 | Wang et al. | |
| 5,882,206 A | 3/1999 | Gillio | |
| 5,887,121 A | 3/1999 | Funda et al. | |
| 5,931,832 A | 8/1999 | Jensen | |
| 5,950,629 A | 9/1999 | Taylor et al. | |
| 6,024,695 A | 2/2000 | Taylor et al. | |
| 6,102,850 A | 8/2000 | Wang et al. | |
| 6,574,355 B2 * | 6/2003 | Green | 382/128 |
| 2002/0140665 A1 | 10/2002 | Gordon | |

FOREIGN PATENT DOCUMENTS

| | | |
|---|---|---|
| EP | 0239409 A1 | 9/1987 |
| EP | 0424687 A1 | 5/1991 |
| EP | A-0494943 | 8/1995 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 97/15240 | 5/1997 |
| WO | WO 98/25666 | 6/1998 |

OTHER PUBLICATIONS

Abstract of a presentation "3-D Vision Technology Applied to Advanced Minimally Invasive Surgery Systems" given at the 3rd World Congress of Endoscopic Surgery in Bordeaux, (Jun. 18 to 20, 1992), entitled "Session 15/3" (1 page total).
Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992 (1 page total).
Abstract of a presentation "Concept and Experimental Application of a Surgical Robotic System the Steerable MIS Instrument SMI" given at the 3rd World Congress of Endoscopic Surgery in Bordeaux, Jun. 18-20, 1992 (1 page total).
Abstract of a presentation given at the 3rd World Congress of Endoscopic Surgery in Bordeaux (Jun. 18 to 20, 1992) entitled "Session 15/2" (1 page total).
Abstract of a presentation given at the 3rd World Congress of Endoscopic Surgery in Bordeaux (Jun. 18 to 20, 1992) entitled "Session 15/5" (1 page total).
Abstract of a presentation given at the 3rd World Congress of Endoscopic Surgery in Bordeaux (Jun. 18 to 20, 1992) entitled "Session 15/4" (1 page total).
Abstract of a presentation given at the 3rd World Congress of Endoscopic Surgery in Bordeaux, (Jun. 18 to 20, 1992) entitled "Session 15/1" (1 page total).
Bejczy, "Controlling Remote Manipulators through Kinesthetic Coupling," Computers in Mechanical Engineering 1983, pp. 48-60.
Besant et al., Abstract of a presentation "Camera Control for Laparoscopic Surgery by Speech-Recognizing Robot: Constant Attention and Better Use of Personnel," given at the 3rd World Congress of Endoscopic Surgery in Bordeaux, Jun. 18-20, 1992 (1 page total).
Charles et al., "Design of a Surgeon-Machine Interface for Teleoperated Microsurgery," IEEE 1989 (3 pages total).

Colgate, "Power and Impedance Scaling in Bilateral Manipulation," IEEE, 1991, pp. 2292-2297.
Corcoran, "Robots for the Operating Room," The New York Times, Sunday Jul. 18, 1992, Section 3, p. 9, col. 1 (2 pages total).
Das et al., "Kinematic Control and Visual Display of Redundant Teleoperators," IEEE 1989 pp. 1072-1077.
Dolan et al., "A Robot in an Operating Room: A Bull in a China Shop," IEEE, 1987, pp. 1096-1097.
Gayed et al., "An Advanced Control Micromanipulator for Surgical Applications," Systems Science vol. 13, 1987, pp. 23-34.
Green et al., Abstract of a presentation "Telepresence: Advanced Teleoperator Technology for Minimally Invasive Surgery," given at "Medicine meets virtual reality" symposium in San Diego, Jun. 4-7, 1992 (20 pages total).
Green et al., Abstract of a presentation "Telepresence: Advanced Teleoperator Technology for Minimally Invasive Surgery," given at the 3rd World Congress of Endoscopic Surgery in Bordeaux, Jun. 18-20, 1992 (2 pages total).
Green, Statutory Declaration of Dr. Philip S. Green, presenter of the video entitled "Telepresence Surgery—The Future of Minimally Invasive Medicine" (32 page total).
Guerrouad et al., "S.M.O.S.: Stereotaxical Microtelemanipulator for Ocular Surgery," IEEE, 1989, pp. 879-880.
Inoue, "Force Feedback-Based Telemicromanipulation for Robot Surgery on Soft Tissues" (A.M. Inoue), IEEE 1989.
Inoue et al., "Six-axis Bilateral Control of an Articulated Slave Manipulator Using a Cartesian Master Manipulator," Advanced Robotics, 4, No. 2, 1990, pp. 138-150.
Kazerooni, "Human/Robot Interaction via the Transfer of Power and Information Signals—Part I: Dynamics and Control Analysis," IEEE, 1989, pp. 1632-1640.
Kazerooni, "Human/Robot Interaction via the Transfer of Power and Information Signals—Part II; An Experimental Analysis," IEEE, 1989, pp. 1641-1647.
Krishnan et al., Abstract of a presentation "Design Considerations of a New Generation Endoscope Using Robotics and Computer Vision Technology," given at the 3rd World Congress of Endoscopic Surgery in Bordeaux, Jun. 18-20, 1992 (1 page total).
Lavallee. "A New System for Computer Assisted Neurosurgery," IEEE, 1989, vol. 11, pp. 923-927.
Mair, Industrial Robotics, Prentice Hall, 1988, pp. 41-43, 49-50, 54, 203-209.
Majima et al.; "On a Micro-Manipulator for Medical Application—Stability Consideration of its Bilateral Controller," Mechatronics, 1991, pp. 293-309.
NASA, "Anthropomorphic Remote Manipulator", NASA Tech Briefs, 1991 (1 page total).
Preising et al., "A Literature Review: Robots in Medicine," IEEE, Jun. 1991, pp. 13-22 & 71.
Taubes, "Surgery In Cyberspace," Discover Magazine, Dec. 1994, pp. 85-92.
Taylor et al., "Taming the Bull: Safety In a Precise Surgical Robot," IEEE, 1991, pp. 865-871.
Tejima, "A New Microsurgical Robot System for Corneal Transplantation," Precision Machinery, 1988 vol. 2, pp. 1-9.
Tendick et al., "Analysis of the Surgeon's Grasp for Telerobotic Surgical Manipulation," IEEE, 1989, pp. 914-915.
Thring, "Robots and Telechire: Manipulator with Memory: Remote Manipulators: Machine Limbs for the Handicapped," Wiley & Sons, 1983 (28 pages total).
Transcript of a video presented by SRI at the 3rd World Congress of Endoscopic Surgery In Bordeaux on Jun. 18-20, 1992, in Washington on Apr. 9, 1992, and in San Diego, CA on Jun. 4-7, 1992 entitled "Telepresence Surgery—The Future of Minimally Invasive Medicine" (3 pages total).
Trevelyan et al., "Motion Control for a Sheep Shearing Robot," Proceedings of the 1st International Symposium on Robotics Research. MIT, Cambridge, Massachusetts, USA, 1983, pp.175-190.
Vibet, "Properties of Master-Slave Robots," Motor-con, 1987, pp. 309-314.
Wolf et al., "Student Reference Manual for Electronic Instrumentation Laboratories," Prentice Hall, New Jersey 1990, pp. 498-499.

* cited by examiner

INTERNAL MAMMARY ARTERY

CORONARY ARTERY

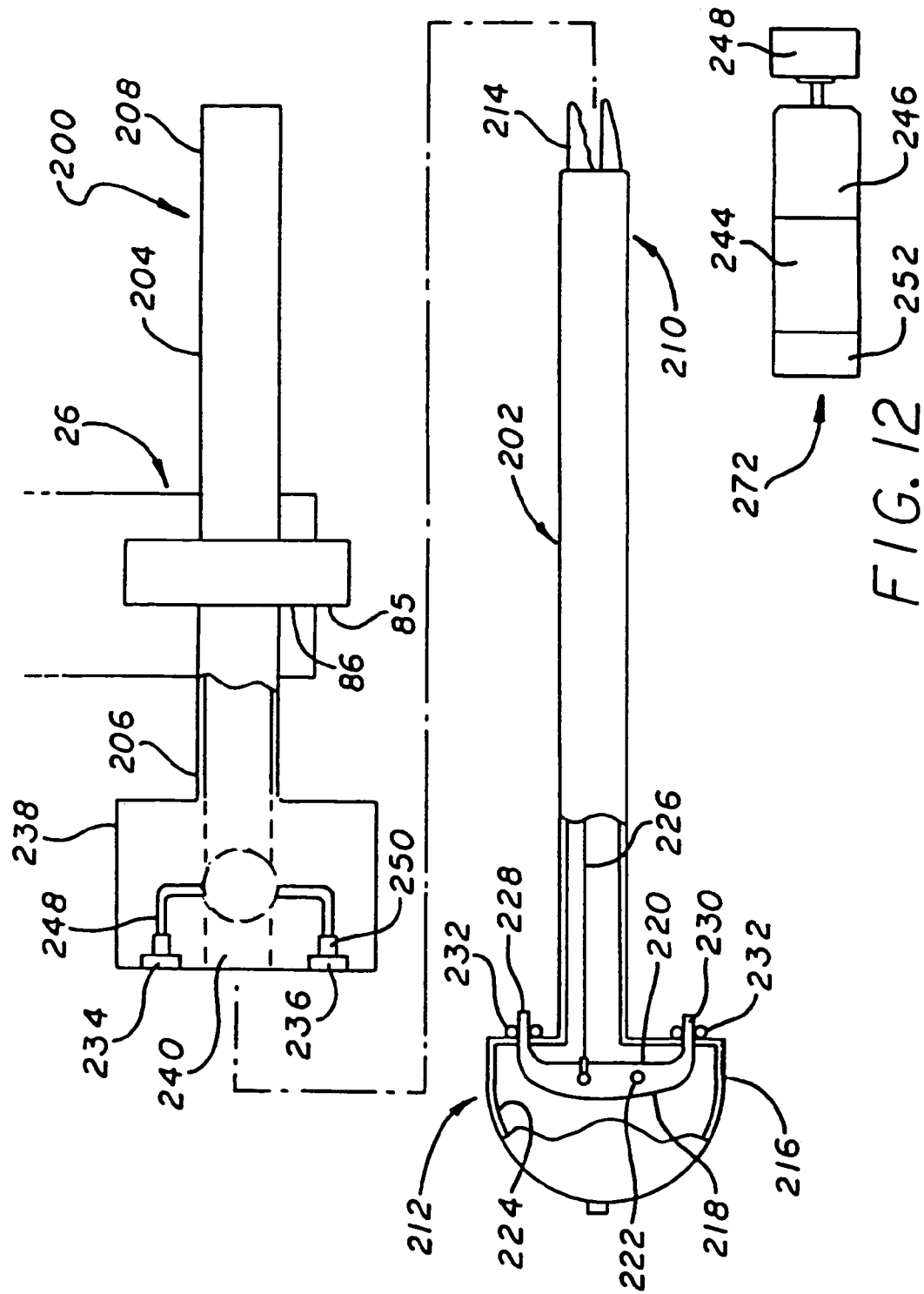

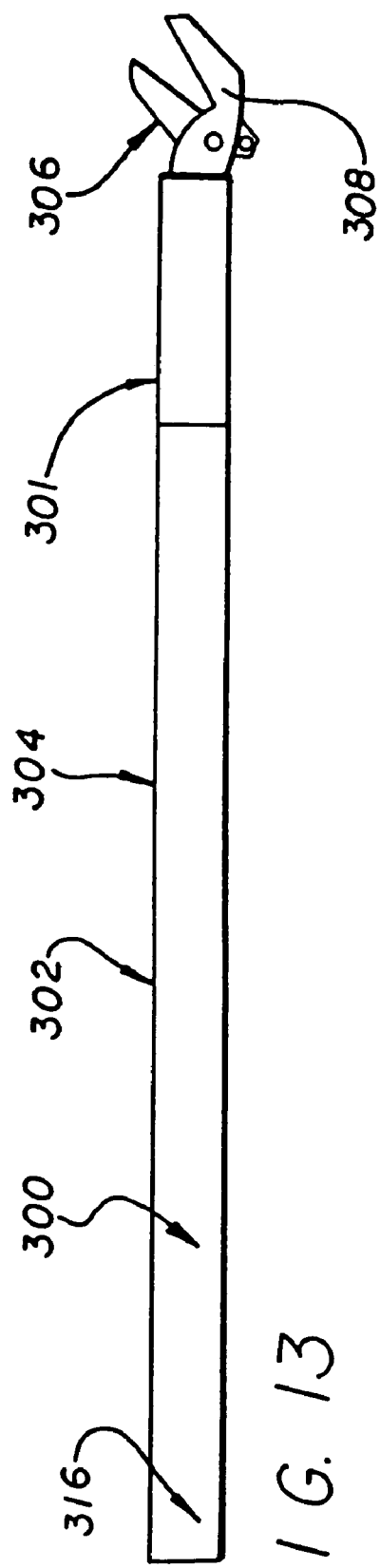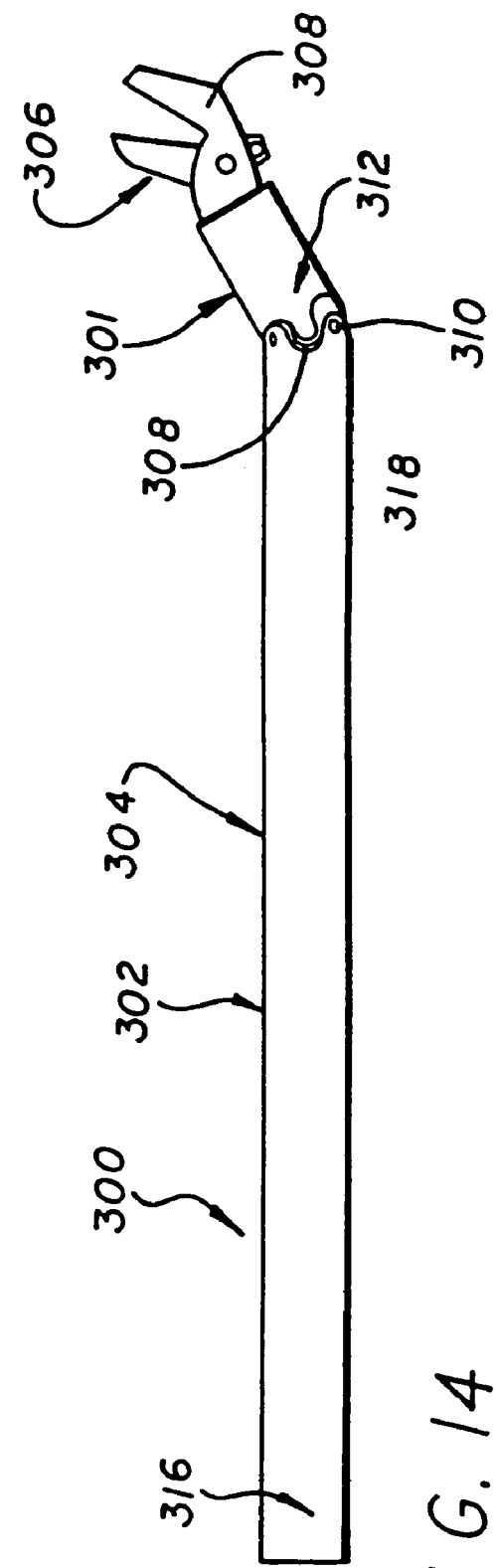
FIG. 13
FIG. 14

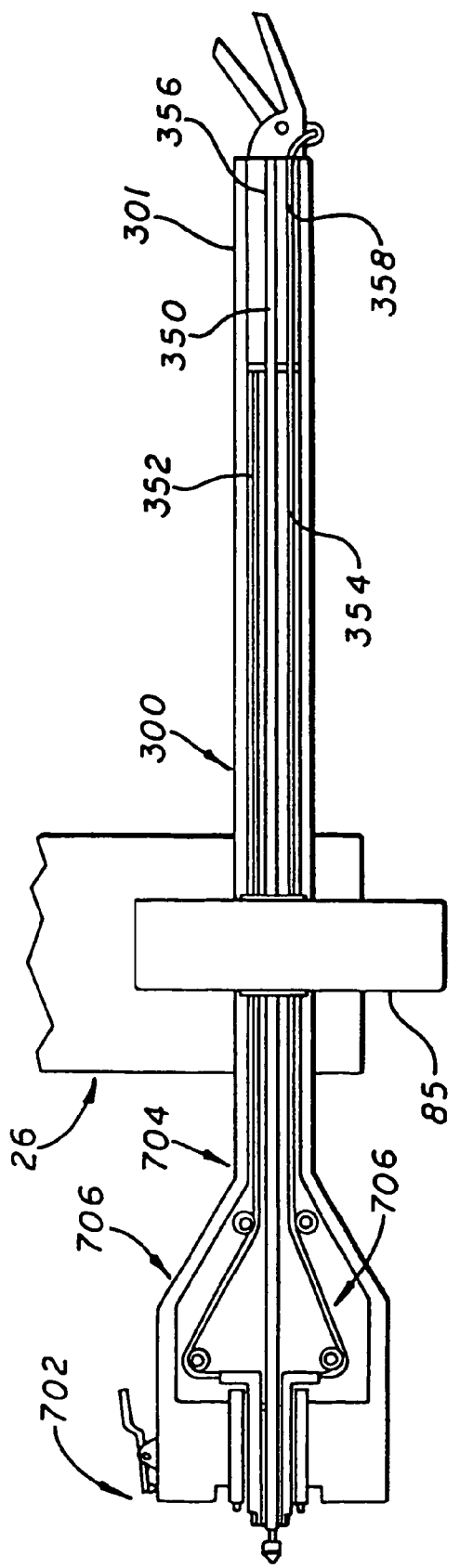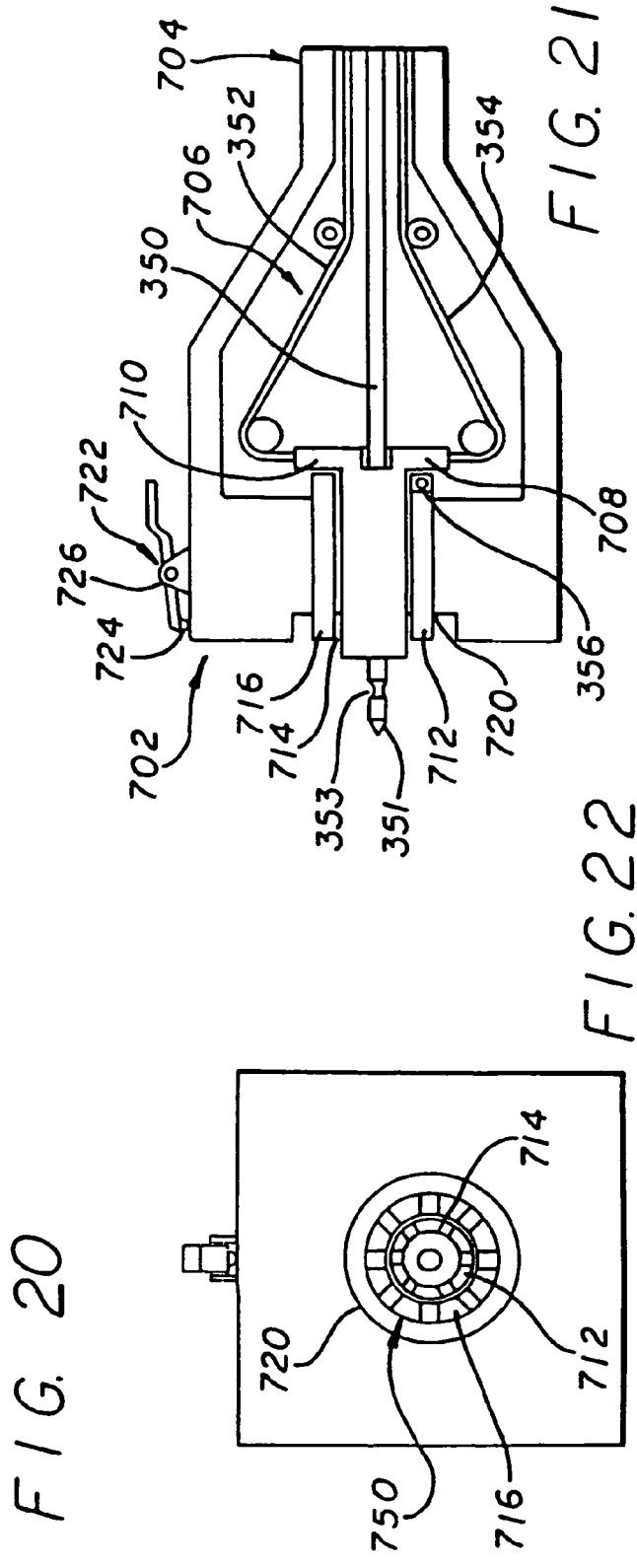

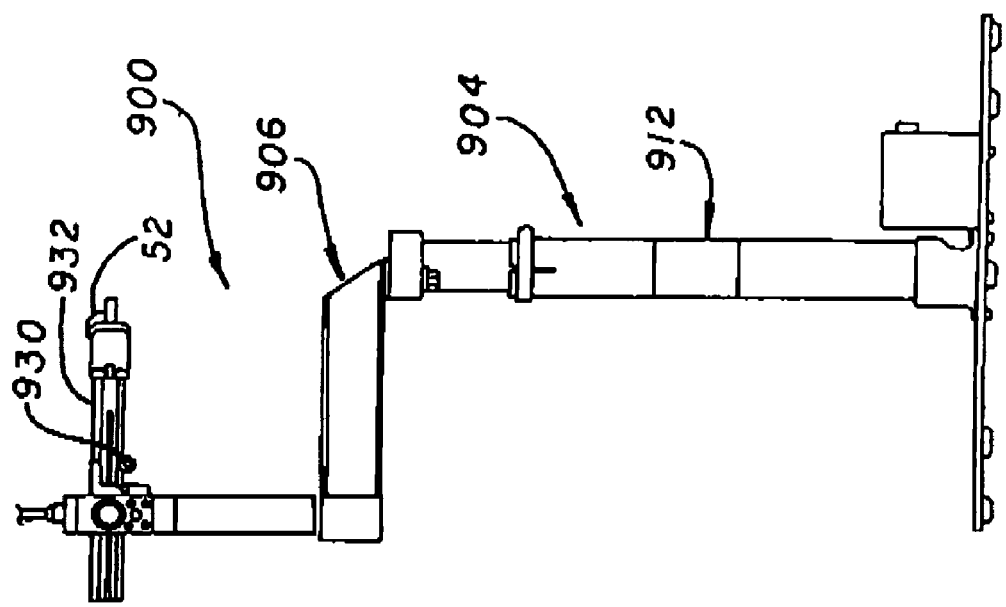
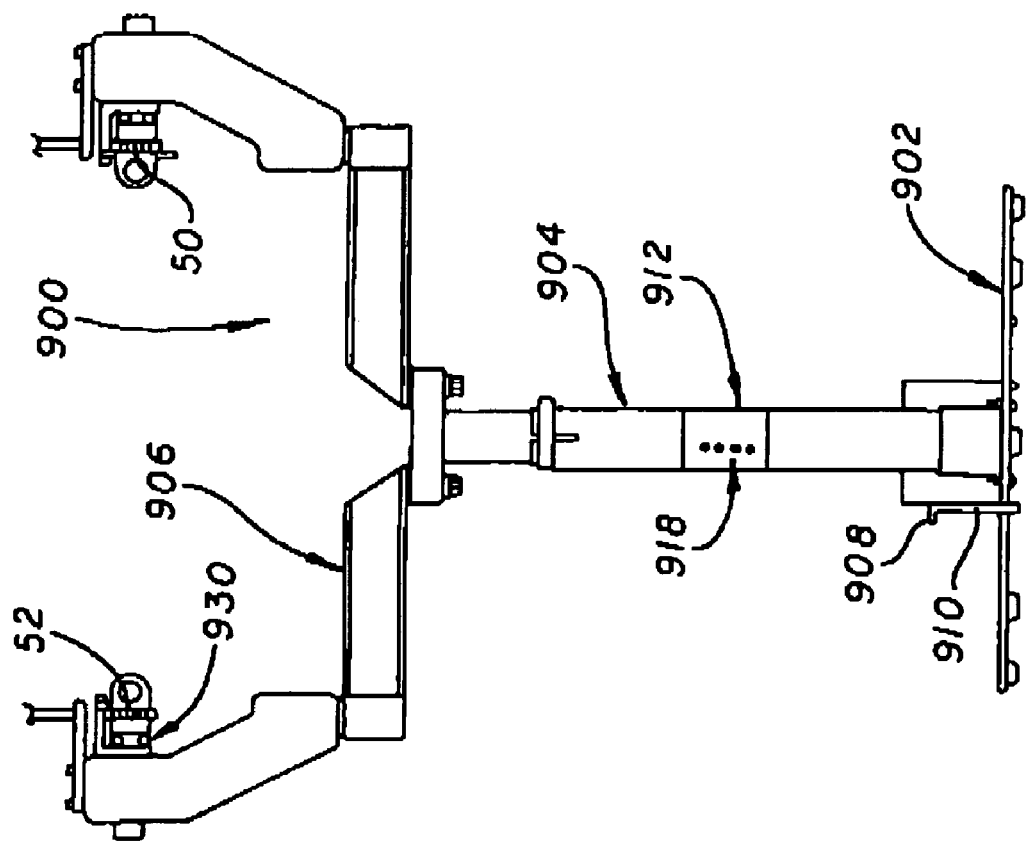

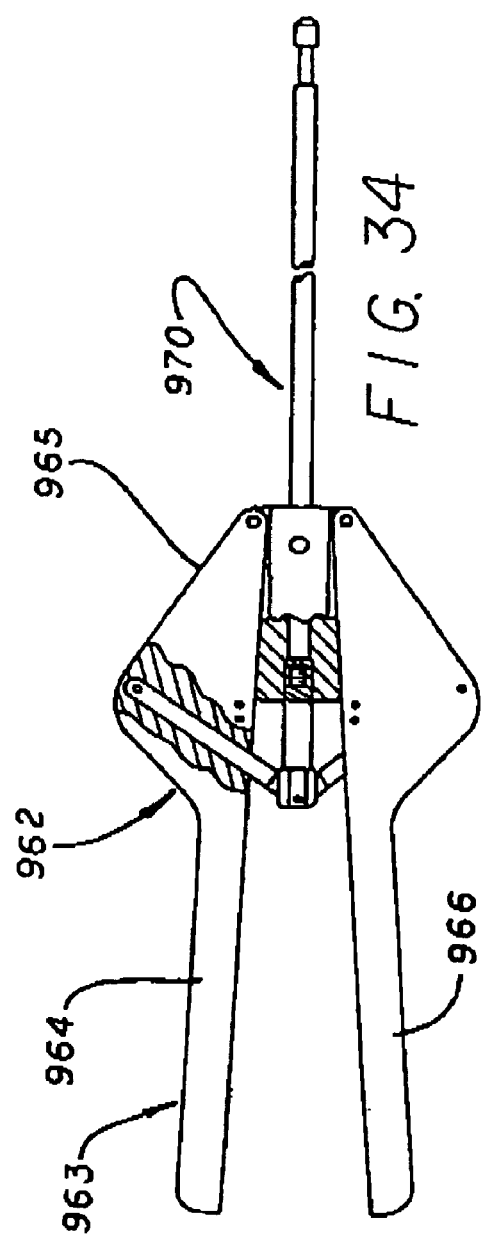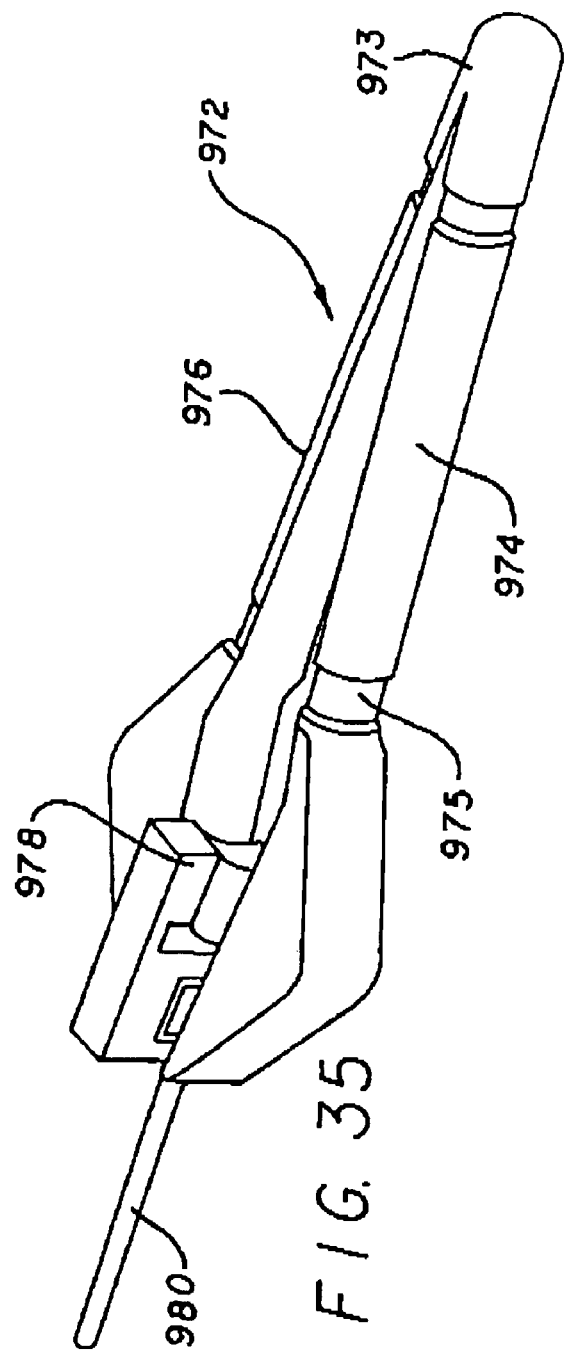

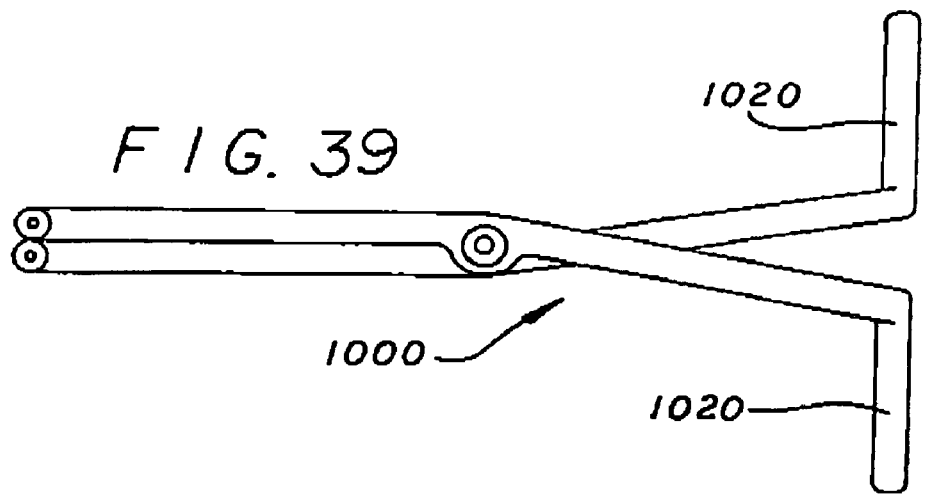
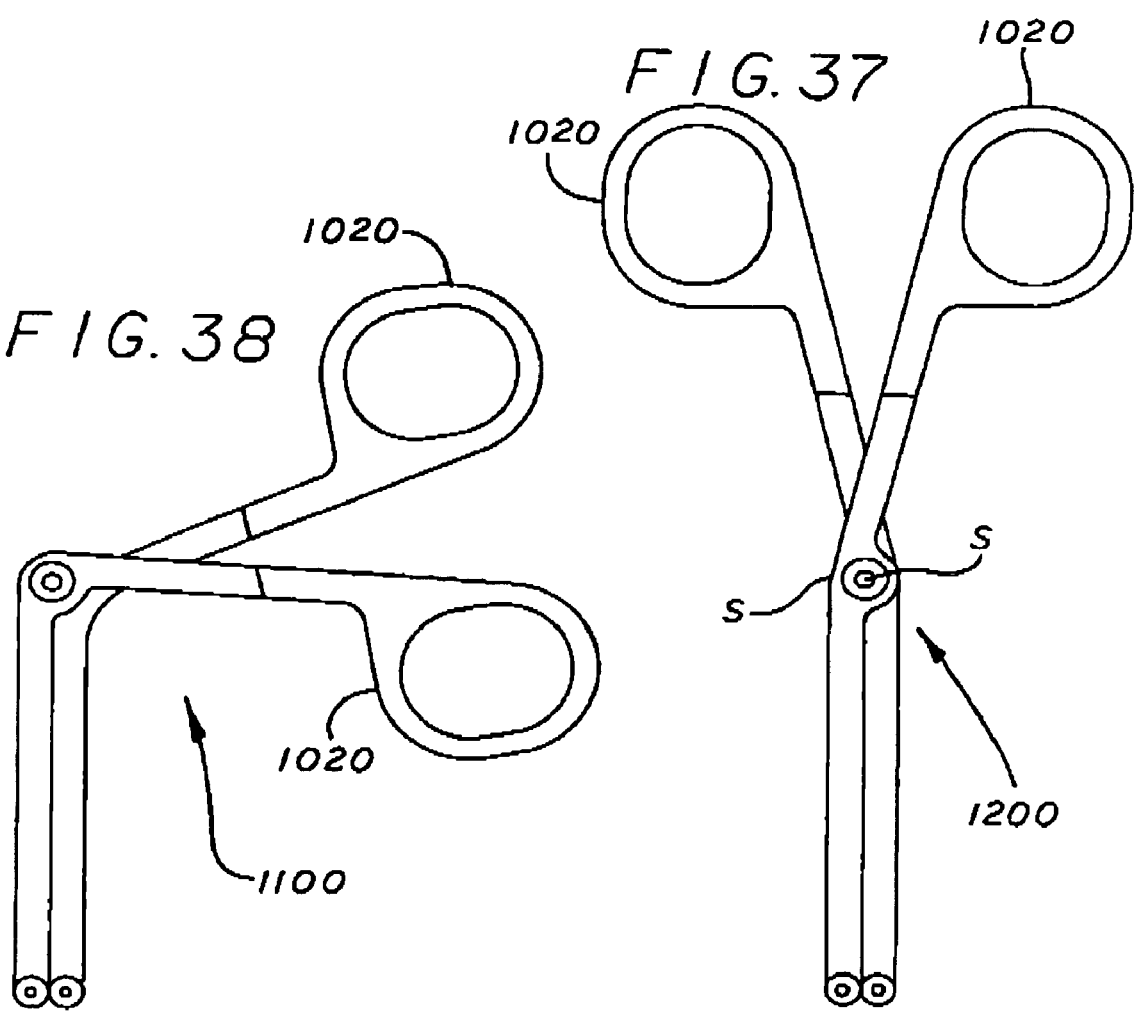

MEDICAL ROBOTIC SYSTEM WITH DIFFERENT SCALING FACTORS

CROSS-REFERENCES TO RELATED APPLICATIONS

The present application is a continuation of application Ser. No. 10/737,195, filed Dec. 15, 2003, now U.S. Pat. No. 7,083,571, which is a continuation application of U.S. patent application Ser. No. 09/557,950 filed Apr. 24, 2000, now U.S. Pat. No. 6,699,177 which is a continuation of Ser. No. 08/873,190 filed Jun. 11, 1997, now U.S. Pat. No. 6,102,177 which is a continuation-in-part Application of U.S. patent application Ser. No. 08/814,811 filed on Mar. 10, 1997, now abandoned and U.S. patent application Ser. No. 08/755,063 filed on Nov. 22, 1996, now U.S. Pat. No. 5,855,583, which is a continuation-in-part Application of U.S. patent application Ser. No. 08/603,543, filed on Feb. 20, 1996, now U.S. Pat. No. 5,762,458. All of the above-referenced references are incorporated herein by reference.

BACKGROUND OF THE INVENTION

1. Field of the Invention

The present invention relates to a system and method for performing minimally invasive cardiac procedures. More particularly, the present invention relates to a robotic system and surgical instruments that may be removably attached thereto, wherein said system aids in performing minimally invasive surgical procedures.

2. Description of Related Art

Blockage of a coronary artery may deprive the heart of the blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery (IMA) is then severed and attached to the artery at the point of incision. The IMA bypasses the blocked area of the artery to again provide a full flow of blood to the heart. Splitting the sternum and opening the chest cavity, commonly referred to as 'open surgery', can create a tremendous trauma on the patient. Additionally, the cracked sternum prolongs the recovery period of the patient.

There have been attempts to perform CABG procedures without opening the chest cavity. Minimally invasive procedures are conducted by inserting surgical instruments and, an endoscope through small incision in the skin of the patient. Manipulating such instruments can be awkward, particularly when suturing a graft to an artery. It has been found that a high level of dexterity is required to accurately control the instruments. Additionally, human hands typically have at least a minimal amount of tremor. The tremor further increases the difficulty of performing minimally invasive cardiac procedures.

To perform MIS, the surgeon uses special instruments. These instruments allow the surgeon to maneuver inside the patient. One type of instrument that is used in minimally invasive surgery is forceps, an instrument having a tip specifically configured to grasp objects, such as needles. Because forceps and other instruments designed for minimally invasive surgery are generally long and rigid, they fail to provide a surgeon the dexterity and precision necessary to effectively carry out many procedures in a minimally invasive fashion. For example, conventional MIS forceps are not well suited for manipulating a needle during a minimally invasive procedure, such as during endoscopy. Therefore, many MIS procedures that might be performed, have, as of yet, not been accomplished.

In essence, during open surgeries, the tips of the various instruments may be positioned with six degrees of freedom. However, by inserting an instrument through a small aperture, such as one made in a patient to effectuate a minimally invasive procedure, two degrees of freedom are lost. It is this loss of freedom of movement within the surgical site that has substantially limited the types of MIS procedures that are performed.

Dexterity is lacking in MIS because the instruments that are used fail to provide the additional degrees of freedom that are lost when the instrument is inserted into a patient. One problem associated with this lack of dexterity is the inability to suture when the instruments are in certain positions. As a result, surgeries that require a great deal of suturing within the surgical site are almost impossible to perform because the surgical instruments to enable much of this work are not available.

Another problem associated with MIS is the lack of precision within the surgical site. For procedures such as the MICABG (Minimally Invasive Coronary Artery Bypass Graft), extremely small sutures must be emplaced in various locations proximate the heart. As such, precise motion of the tool at the tip of a surgical instrument is necessary. Currently, with hand positioned instruments, the precision necessary for such suturing is lacking.

As such, what is needed in the art is a tool and class of surgical instruments that may be articulated within the patient such that a surgeon has additional degrees of freedom available to more dexterously and precisely position the tool at the tip of the instrument, as is needed.

Additionally, what is needed in the art is a method and mechanism that provides simple handle, instrument and tool changing capabilities so that various tools may be easily and readily replaced to enable faster procedures to thus minimize operating room costs to the patient and to lessen the amount of time a patient is under anesthesia.

It is to the solution of the aforementioned problems to which the present invention is directed.

BRIEF SUMMARY OF THE INVENTION

The present invention is a system for performing minimally invasive surgical procedures, and more particularly, minimally invasive cardiac procedures. The system includes a pair or more of surgical instruments that are coupled to a pair or more of robotic arms. The system may include only a single surgical instrument and a single robotic arm as well and as is hereinbelow disclosed. The instruments have end effectors that can be manipulated to sever, grasp, cauterize, irradiate and suture tissue. Each robotic arm is coupled to a master handle by a controller. The robotic arms may be selectively connected to a specific master handle such that a surgeon may selectively control one or more of a plurality of robotic arms. The handles can be moved by the surgeon to produce a corresponding movement of the end effectors and the surgical tools attached thereto. The movement of the handles is scaled so that the end effectors have a corresponding movement that is different, typically smaller, than the movement performed by the hands of the surgeon. This helps in removing any tremor the surgeon might have in their hands. The scale factor is adjustable so that the surgeon can control the resolution of the end effector movement. The scale factor may be effectuated via a voice recognition system, control buttons or the like. The movement of the end effector can be controlled by an input button, so that the end effector only moves when the button is depressed or toggled by the surgeon. Alternatively, the movement can be activated via voice control in a manner similar to the scaling factor adjustment set out hereinbelow. The input button allows the surgeon to adjust the position of the handles without moving the end effector, so that the handles can be moved to a more comfortable position. The system may also have a robotically controlled endoscope which allows the surgeon to remotely view the surgical site. A cardiac procedure can be performed by making small incisions in the patient's skin and inserting the instruments and endoscope into the patient. The surgeon manipulates the handles and moves the end effectors to perform a cardiac procedure such as a coronary artery bypass graft or heart valve surgery.

The present invention is additionally directed to a surgical instrument and method of control thereof which permits the surgeon to articulate the tip of the instrument, while retaining the function of the tool at the tip of the instrument. As such, the instrument tip may be articulated with two degrees of freedom, all the while the tool disposed at the tip may be used.

The robotic system generally comprises: a robotic arm; a coupler attached to the arm; a surgical instrument that is held by the coupler; a controller; and wherein movement at the controller produces a proportional movement of the robotic arm and surgical instrument.

The present invention may include a surgical instrument that has an elongated rod. The elongated rod has a longitudinal axis and generally serves as the arm of the endoscopic instrument. An articulate portion is mounted to and extends beyond the elongated rod. Alternatively, the articulate portion may be integrally formed with the elongated rod. The articulate portion has a proximal portion, a pivot linkage and a distal portion. The proximal portion may include a pair of fingers. The fingers may be orthogonal to each other and oriented radially to the longitudinal axis of the elongated rod. For use in surgical procedures, it is generally preferable that the instrument and the majority of the components therein are formed of stainless steel, plastic, or some other easily steralizable material. Each of the fingers may have at least one aperture formed therein to allow the passage of a pin which aids in the attachment of the pivot linkage to the proximal portion of the articulate portion and which allows the pivot linkage to be pivotally mounted to the proximal portion. The articulate portion provides articulation at the tip of an instrument that includes the articulate portion. More particularly, this provides additional degrees of freedom for the tool at the tip of an instrument that includes an articulate portion.

An instrument such as that disclosed hereinbelow, when used in conjunction with the present surgical system, provides the surgeon additional dexterity, precision, and flexibility not yet achieved in minimally invasive surgical procedures. As such, operation times may be shortened and patient trauma greatly reduced.

To provide increased precision in positioning the articulated tip as disclosed hereinbelow, there is provided two additional degrees of freedom to the master controller. Each of the two additional degrees of freedom are mapped to each of the degrees of freedom at the instrument tip. This is accomplished through the addition of two joints on the master and automatic means for articulating the instrument tip in response to movements made at the master.

The objects and advantages of the present invention will become more readily apparent to those ordinarily skilled in the art after reviewing the following detailed description and drawings wherein:

BRIEF DESCRIPTION OF THE DRAWINGS

FIG. 8a is a side view of the master handle of the system in accordance with the present invention;

FIG. 11 is a side view of a rear-loading tool driver in accordance with the system of the present invention;

FIG. 12 is a plan view of the motor assembly of the back loading tool driver of FIG. 11;

FIG. 13 is a side plan view of an articulable instrument in accordance with the present invention;

FIG. 14 is a side plan view of an articulable instrument, where the instrument tip is articulated;

FIG. 20 is a cross-sectional view of an articulable instrument attached to the articulate-translator of the present invention;

FIG. 21 is a close-up cross section view of the articulate-translator in accordance with the present invention;

FIG. 22 is an end view of the articulate translator in accordance with the present invention;

FIG. 31 is a plan view of an alternative master-handle console in accordance the present invention;

FIG. 32 is a plan view of an alternative master-handle console in accordance with the present invention;

FIG. 34 is a partial cut-away plan view of a handle in accordance with the present invention;

FIG. 35 is a perspective view of an alternative embodiment of a handle in accordance with the present invention;

FIG. 37 is an alternative embodiment of a handle in accordance with the present invention;

FIG. 38 is an alternative embodiment of a handle in accordance with the present invention; and FIG. 39 is an alternative embodiment of a handle in accordance with the present invention.

DETAILED DESCRIPTION OF THE INVENTION

Figure 1:
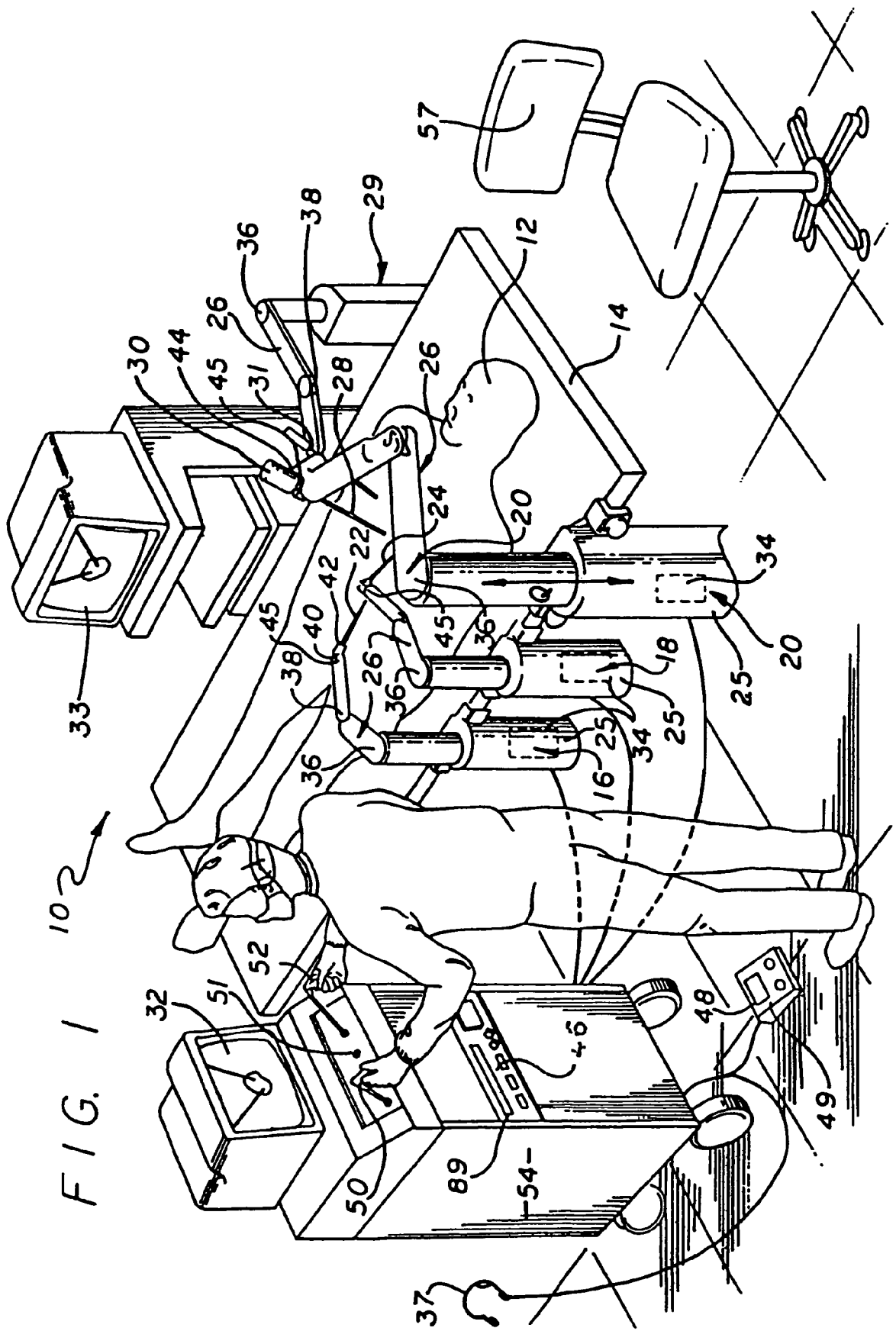
FIG. 1 is a perspective view of a minimally invasive surgical system in accordance with the present invention.

Referring to the drawings more particularly by reference numbers, FIG. 1 shows a system 10 that can be used to perform minimally invasive surgery. In a preferred embodiment, the system 10 may be used to perform a minimally invasive coronary artery, bypass graft, or Endoscopic coronary artery bypass graft (E-CABG) and other anastomostic procedures. Although a MI-CABG procedure is shown and described, it is to be understood that the system may be used for other surgical procedures. For example, the system can be used to suture any pair of vessels as well as cauterizing, cutting, and radiating structures within a patient.

The system 10 is used to perform a procedure on a patient 12 that is typically lying on an operating table 14. Mounted to the operating table 14 is a first articulate arm 16, a second articulate arm 18 and a third articulate arm 20. The articulate arms 16-20 are preferably mounted to the table so that the arms are in a plane proximate the patient. It is to be appreciated that the arms may be mounted to a cart or some other device that places the arms proximate the plane of the patient as well. Although three articulate arms are shown and described, it is to be understood that the system may have any number of arms, such as one or more arms.

The first and second articulate arms 16 and 18 each have a base housing 25 and a robotic arm assembly 26 extending from the base housing 25. Surgical instruments 22 and 24 are preferably removably coupled at the end of each robotic arm assembly 26 of the first and second articulate arms 16, 18. Each of the instruments 22, 24 may be coupled to a corresponding robotic arm assembly 26 in a variety of fashions which will be discussed in further detail hereinbelow.

The third articulate arm 20 additionally comprises a base housing 25 and a robotic arm assembly 26, and preferably has an endoscope 28 that is attached to the robotic arm assembly 26. The base housing 25 and robotic arm assemblies 26 of each of the articulate arms 16, 18, and 20 are substantially similar. However, it is to be appreciated that the configuration of the third articulate arm 20, may be different as the purpose of the third articulate arm is to hold and position the endoscope 28 as opposed to hold and position a surgical instrument. Additionally, a fourth arm 29 may be included in the system 10. The fourth arm 29 may hold an additional instrument 31 for purposes set out hereinbelow.

The instruments 22, 24 and 29 and endoscope 28 are inserted through incisions cut into the skin of the patient 12. The endoscope 28 has a camera 30 that is coupled to a monitor 32 which displays images of the internal organs of the patient 12.

Each robotic arm assembly 26 has a base motor 34 which moves the arm assembly 26 in a linear fashion, relative to the base housing 25, as indicated by arrows Q. Each robotic arm assembly 26 also includes a first rotary motor 36 and a second rotary motor 38. Each of the robotic arm assemblies 26 also have a pair of passive joints 40 and 42. The passive joints 40, 42 are preferably disposed orthogonal to each other to provide pivotal movement of the instrument 22, 24 or endoscope 28 that is attached to a corresponding robotic arm assembly 26. The passive joints may be spring biased in any specific direction, however, they are not actively motor driven. The joint angle is controlled to a particular value using a feedback control loop. The robotic arm assemblies 26 also have a coupling mechanism 45 to couple the instruments 22 and 24, or endoscope 28 thereto. Additionally, each of the robotic arm assemblies 26 has a motor driven worm gear 44 to rotate the instrument 22, 24 or endoscope 28 attached thereto about its longitudinal axis. More particularly, the motor driven worm gear spins the instruments or endoscope.

The first, second, and third articulate arms 16, 18, 20 as well as the fourth arm 29 are coupled to a controller 46' which can control the movement of the arms. The arms are coupled to the controller 46 via wiring, cabling, or via a transmitter/receiver system such that control signals may be passed form the controller 46 to each of the articulate arms 16, 18, and 20. It is preferable, to ensure error free communication between each of the articulate arms 16, 18, 20 and 29 and the controller 46 that each arm 16, 18, 20 and 29 be electrically connected to the controller, and for the purposes of example, each arm 16, 18, 20 and 29 is electrically connected to the controller 46 via electrical cabling 47. However, it is possible to control each of the arms 16, 18, 20 and 29 remotely utilizing well-known remote control systems as opposed to direct electrical connections. As such remote control systems are well-known in the art, they will not be further discussed herein.

The controller 46 is connected to an input device 48 such as a foot pedal, hand controller, or voice recognition unit. For purposes of example, a foot controller and voice recognition unit are disclosed herein. The input device 48 can be operated by a surgeon to move the location of the endoscope 28 and view a different portion of the patient by depressing a corresponding button(s) disposed on the input device 48. Alternatively, the endoscope 28 may be positioned via voice control. Essentially, a vocabulary of instructions to move the endoscope, such as up, down, back, and in may be recognized via a speech recognition system and the appropriate instructions are sent to the controller. The speech recognition system may be any well-known speech recognition software. Additionally, the controller 46 includes a vocabulary of appropriate words that may be used with the system 10. Including such a vocabulary in the controller 46 may be accomplished through the inclusion of the aforementioned speech recognition software. To effectuate the voice recognition a microphone 37 is included in the system 10. The microphone 37 may be part of a digital system such that integrity of the signal is ensure.

The controller 46 receives the input signals from the input device; 48 and moves the endoscope 28 and robotic arm assembly 26 of the third articulate arm 20 in accordance with the input commands of the surgeon. Each of the robotic arm assemblies 26 may be devices that are sold by the assignee of the present invention, Computer Motion, Inc. of Goleta, Calif., under the trademark AESOP. The system is also described in U.S. Pat. No. 5,515,478, which is hereby incorporated by reference. Although a foot pedal 49 is shown and described, it is to be understood that the system may have other input means such as a hand controller, or a speech recognition interface.

The movement and positioning of instruments 22, 24 attached to the first and second articulate arms 16 and 18 is controlled by a surgeon at a pair of master handles 50 and 52. Each of the master handles 50, 52 which can be manipulated by the surgeon, has a master-slave relationship with a corresponding one of the articulate arms 16, 18 so that movement of a handle 50 or 52 produces a corresponding movement of the surgical instrument 22, 24 attached to the articulate arm 16, 18. Additionally, a switch 51 may be included in the system 10. The switch 51 may be used by the surgeon to allow positioning of the fourth arm 29. This is accomplished because the position of the switch 51 allows the surgeon to select which of the arms a specific handle 50 or 52 controls. In this way, a pair of handles 50 and 52 may be used to control a plurality of robotic arms. The switch 51 may be connected to a multiplexer to act as a selector so that output from the multiplexer is transmitted to the appropriate robotic arm. Alternatively, the switch may have several positions and may, therefore, direct its output to the appropriate input on the controller 46.

The handles 50 and 52 may be mounted to a portable cabinet 54. A second television monitor 56 may be placed onto the cabinet 54 and coupled to the endoscope 28 via well-known means so that the surgeon can readily view the internal organs of the patient 12. The handles 50 and 52 are also coupled to the controller 46. The controller 46 receives input signals from the handles 50 and 52, computes a corresponding movement of the surgical instruments, and provides output signals to move the robotic arm assemblies 26 and instruments 22, 24. Because the surgeon may control the movement and orientation of the instruments 22, 24 without actually holding the ends of the instruments, the surgeon may use the system 10 of the present invention both seated or standing. One advantage of the present system is that a surgeon may perform endoscopic surgeries in a sitting position. This helps reduce surgeon fatigue and may improve performance and outcomes in the operating room, especially during those procedures that are many hours in length. To accommodate a seated position, a chair 57 may be provided with the system.

Figure 33:
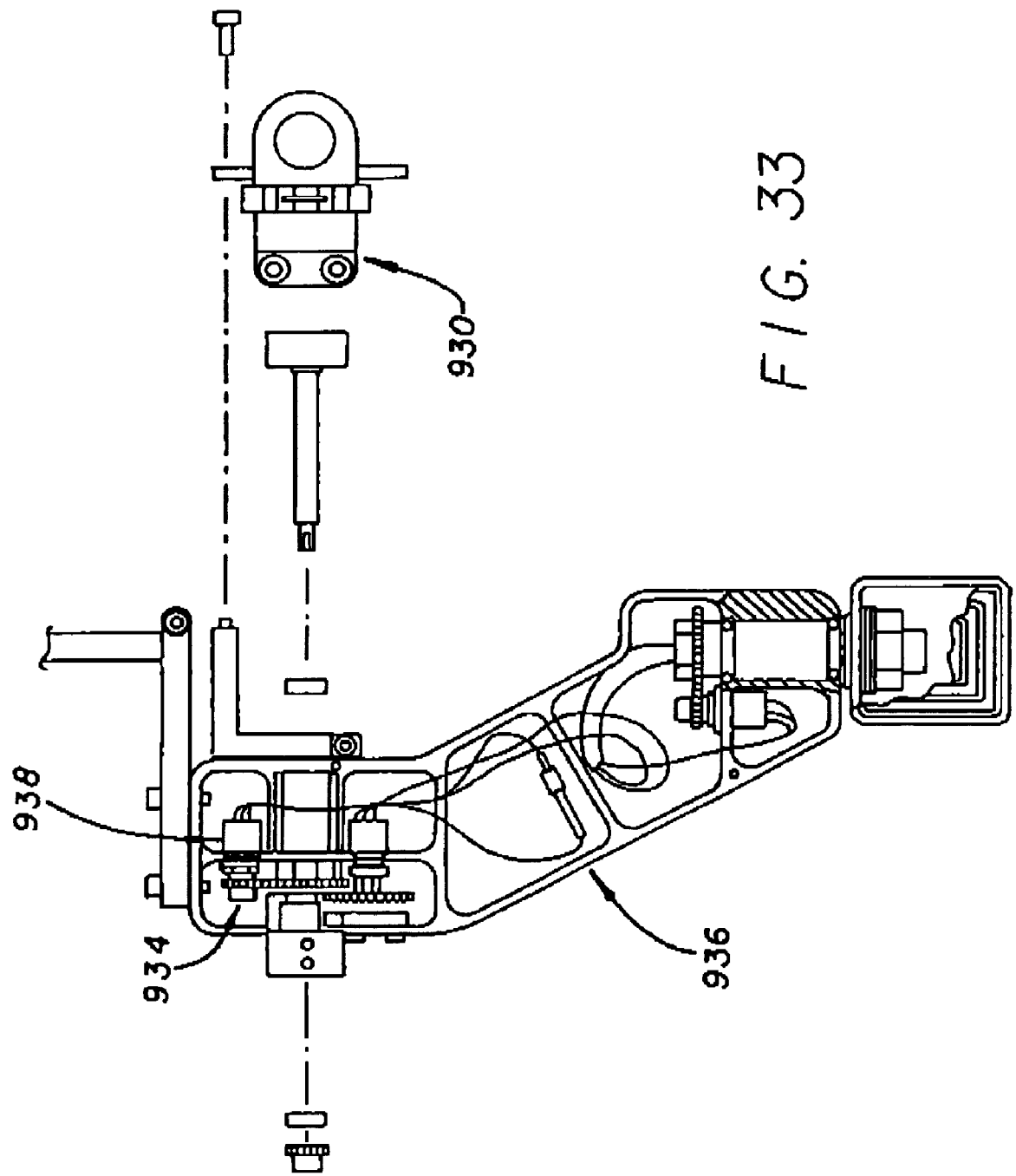
FIG. 33 is a partial cut away cross-section of the master handle console in accordance with the present invention.
Figure 36A:
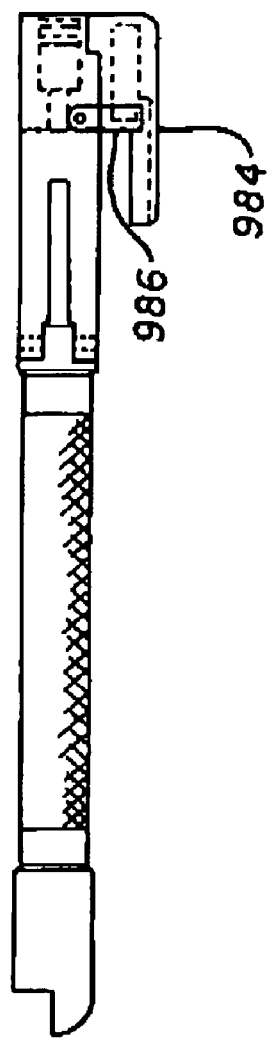
FIG. 36 is a top plan cross-sectional view of the handle depicted in FIG. 35.
Figure 36:
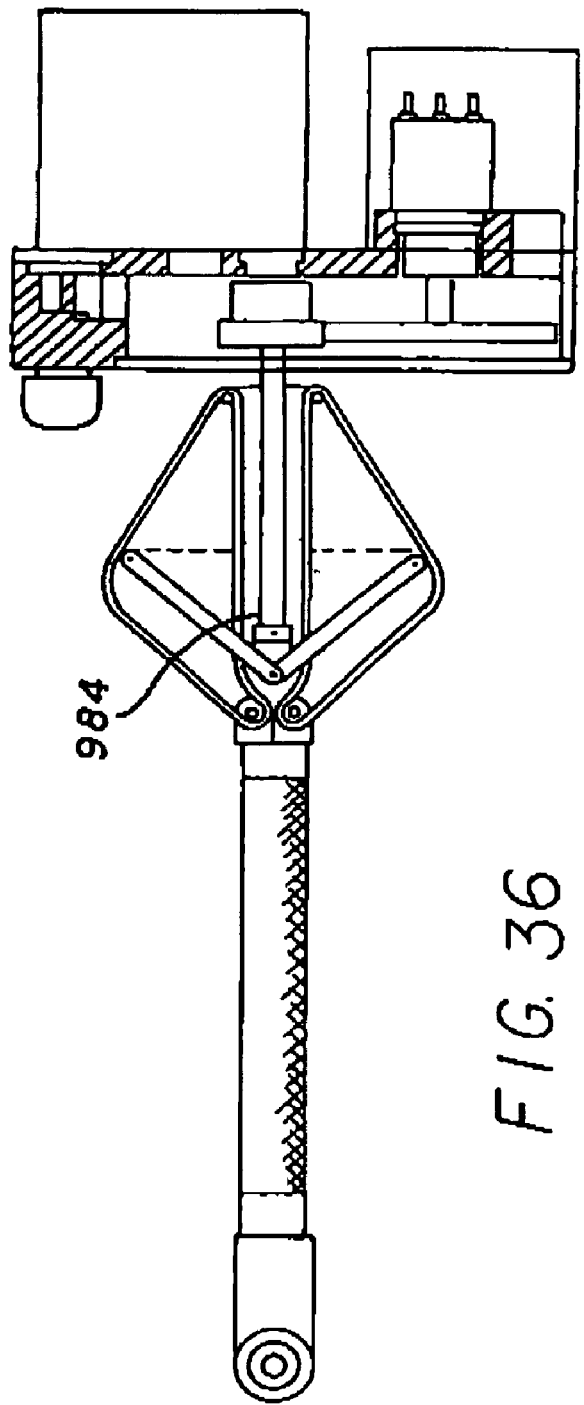

Alternatively, and as depicted in FIGS. 31-33, the handles 50 and 52 may be mounted to a handle stand 900. The handle stand 900 essentially provides for adjustment of the height and tilt of the handles 50 and 52. The handle stand 900 includes a base 902, a neck 904 and a handle portion 906. The base 902 may be adjusted so that the handle stand 900 is tilted. A lever 908 connected to an elongated rod 910 may provide a means for tilting the handle stand 900. As such, the stand 900 may be tilted such that a surgeon using the system 10 can remain comfortable standing or sitting while manipulating the handles 50 and 52.

Additionally, the handle stand 900 may be heightened or shortened depending upon the position of the surgeon (i.e. standing or sitting). This is accomplished via a telescoping section 912. The telescoping section 912 includes an upper portion 914 telescopingly housed within a lower portion 916. A spring biased detent 918 is attached to the upper portion 914 and a plurality of apertures 920 are provided in the lower portion 916 such that the detent 918 seats in an associated aperture 920. The upper portion 914 may be extended by depressing the detent 918 and pulling up on the stand 900. Alternatively, the stand 900 may be lowered by depressing the detent and pushing down on the stand 900. The telescoping section 912 and associated mechanisms serve as a means to raise and lower the stand 900.

Additionally, and as depicted in FIGS. 31-33, the handles 50 and 52 may be attached to the stand 900 via a plurality of rollers 930 and an elongated rod 932. Motion of the rod 932 is transmitted to a plurality of gears 934 disposed on the stand 900. The gears 934 may be housed within a housing 936 to protect them from the environment and to preclude access thereto. Additionally, potentiometers 938 are utilized to measure the position of the handles 50 and 52 relative to a starting position. This will be discussed in more detail hereinbelow. It is to be appreciated that the present invention may be accomplished either utilizing a cabinet 54 or a stand 900. As the handles 50 and 52 are connected to the controller 46 in either case.

Figure 2:
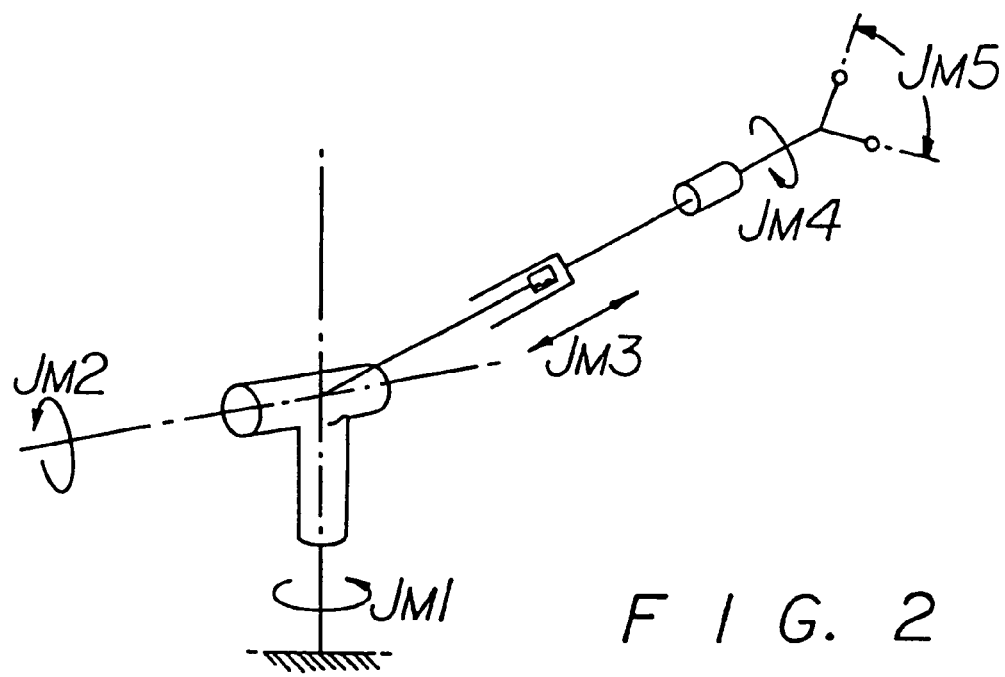
FIG. 2 is a schematic of a master of the system.

Each handle has multiple degrees of freedom provided by the various joints Jm1-Jm5 depicted in FIG. 2. Joints Jm1 and Jm2 allow the handle to rotate about a pivot point in the cabinet 54 or on the stand 900. Joint Jm3 allows the surgeon to move the handle into and out of the cabinet 54 in a linear manner or in a similar manner on the stand 900. Joint Jm4 allows the surgeon to rotate the master handle about a longitudinal axis of the handle. The joint Jm5 allows a surgeon to open and close a gripper.

Each joint Jm1-Jm5 has one or more position sensors which provides feedback signals that correspond to the relative position of the handle. The position sensors may be potentiometers, or any other feedback device such as rotary optical encoders that provides an electrical signal which corresponds to a change of position. Additionally, a plurality of position sensors may be emplaced at each joint to provide redundancy in the system which can be used to alert a surgeon of malfunctions or improper positioning of a corresponding robotic arm assembly 26.

In addition to position sensors, each joint may include tachometers, accelerometers, and force sensing load cells, each of which may provide electrical signals relating to velocity, acceleration and force being applied at a respective joint. Additionally, actuators may be included at each joint to reflect force feed back received at a robotic arm assembly 26. This may be especially helpful at joint jm5 to indicate the force encountered inside a patient by the gripper disposed-at the end of one of the tools 22, or 24. As such, a force reflective element must be included at the gripper of the instrument 22, 24 to effectuate such a force reflective feedback loop. Force reflective elements, such as a piezoelectric element in combination with a whetstone bridge are well-known in the art. However, it is not heretofore know to utilize such force reflection with such a system 10.

Figure 3:
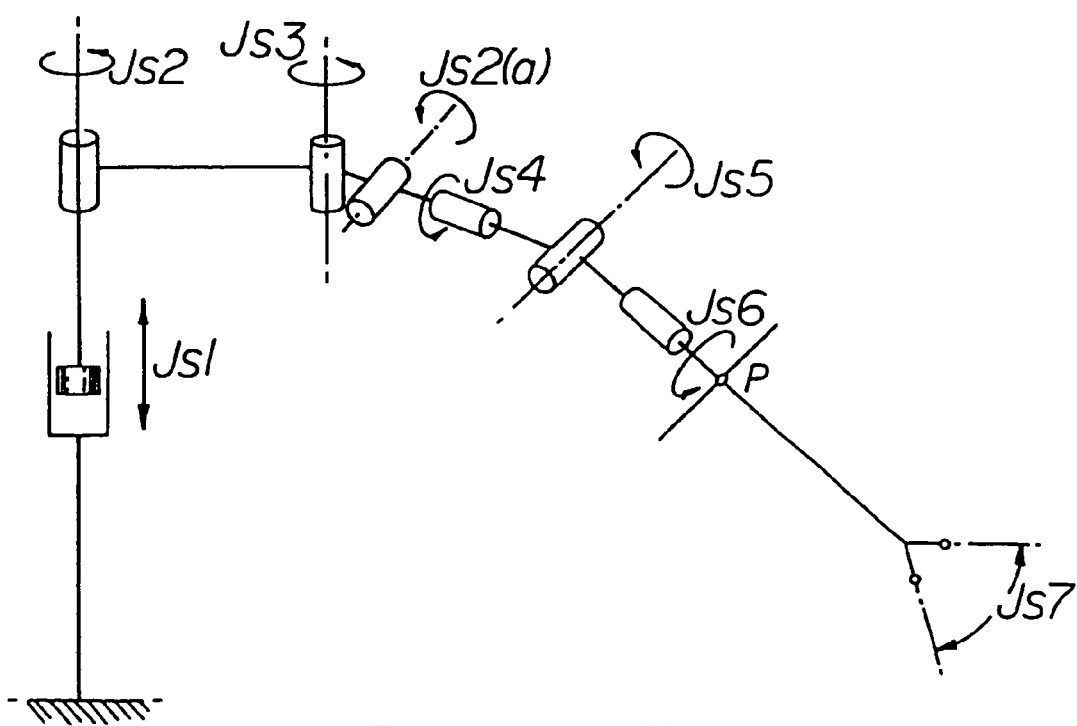
FIG. 3 is a schematic of a slave of the system.

FIG. 3 shows the various degrees of freedom of each articulate arm 16 and 18. The joints Js1, Js2 and Js3 correspond to the; axes of movement of the base motor 34 and rotary motors 36, 38 of the robotic arm assemblies 26, respectively. The joints Js4 and Js5 correspond to the passive joints 40 and 42 of the arms 26. The joint Js6 may be a motor which rotates the surgical instruments about the longitudinal axis of the instrument. The joint Js7 may be a pair of fingers that can open and close. The instruments 22 and 24 move about a pivot point P located at the incision of the patient.

Figure 4:
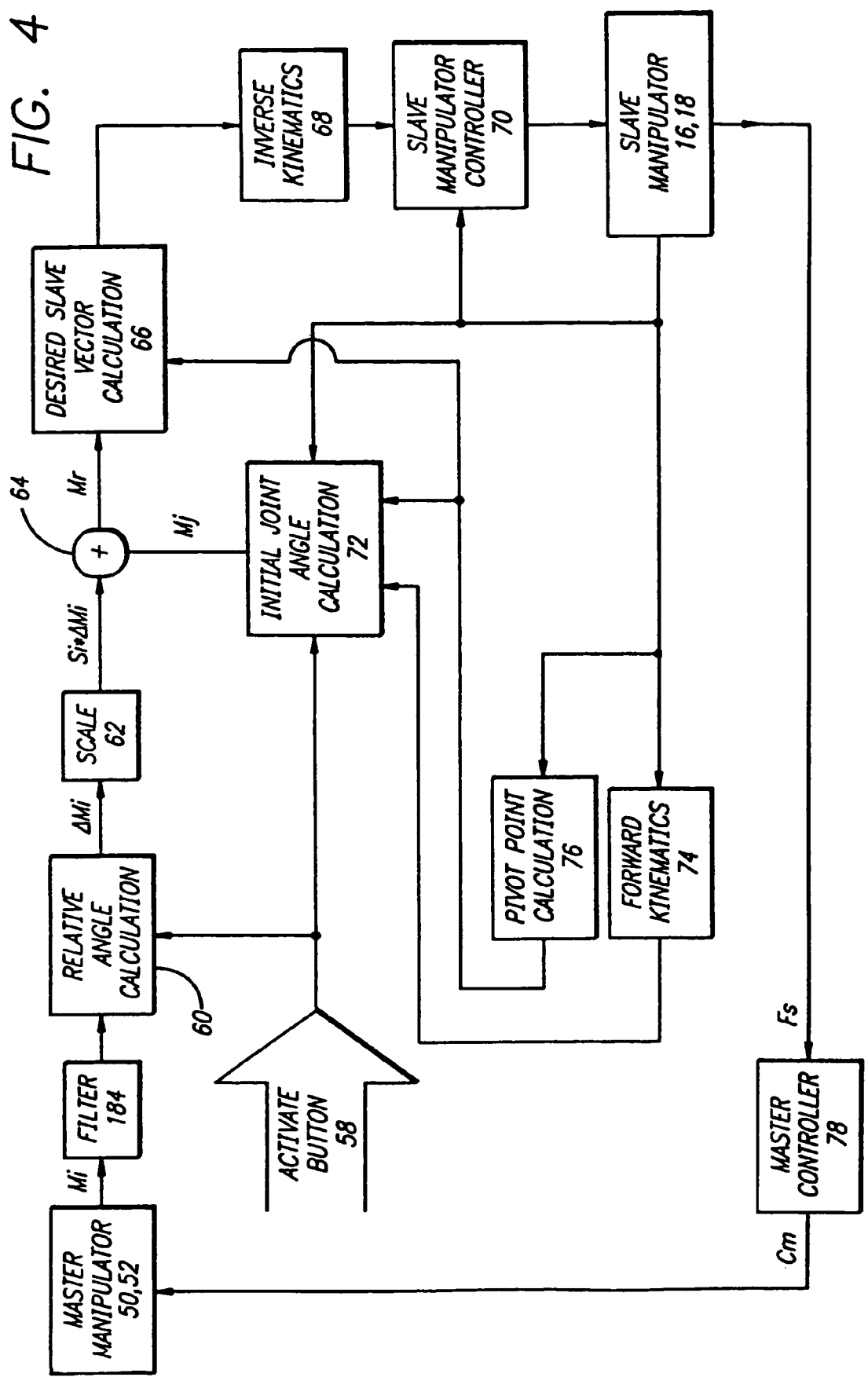
FIG. 4 is a schematic of a control system of the system.

FIG. 4 shows a schematic of a control system that translates a movement of a master handle into a corresponding movement of a surgical instrument. In accordance with the control system shown in FIG. 4, the controller 46 computes output signals for the articulate arms so that the surgical instrument moves in conjunction with the movement of the handle. Each handle may have an input button 58 which enables the instrument to move with the handle. When the input button 58 is depressed the surgical instrument follows the movement of the handle. When the button 58 is released the instrument does not track the movement of the handle. In this manner the surgeon can adjust or "ratchet" the position of the handle without creating a corresponding undesirable movement of the instrument. The "ratchet" feature allows the surgeon to continuously move the handles to more desirable positions without altering the positions of the arms. Additionally, because the handles are constrained by a pivot point the ratchet feature allows the surgeon to move the instruments beyond the dimensional limitations of the handles. Although an input button 58 is shown and described, it is to be understood that the surgical instrument may be activated by other means such as voice recognition. Using the voice recognition would require a specifically vocabulary such as "AWAKE" and "SLEEP" or some other two words having opposing meanings. Voice recognition is well known in general, and it is the specific use of voice recognition in this system 10 that has substantial novelty and utility.

The input button may alternatively be latched so that movement of the corresponding instrument toggles between active and inactive each time the button is depressed by the surgeon.

When the surgeon moves a handle, the position sensors provide feedback signals M1-M5 that correspond to the movement of the joints Jm1-Jm5, respectively. The controller 46 computes the difference between the new handle position and the original handle position in computation block 60 to generate incremental position values s_M1-_M5.

The incremental position values M1-_M5 are multiplied by scale factors S1-S5, respectively in block 62. The scale factors are typically set at less than one so that the movement of the instrument is less than the movement of the handle. In this manner the surgeon can produce very fine movements of the instruments with relatively coarse movements of the handles. The scale factors S1-S5 are variable so that the surgeon can vary the resolution of instrument movement. Each scale factor is preferably individually variable so that the surgeon can more finely control the instrument in certain directions. By way of example, by setting one of the scale factors at zero the surgeon can prevent the instrument from moving in one direction. This may be advantageous if the surgeon does not want the surgical instrument to contact an organ or certain tissue located in a certain direction relative to the patient. Although scale factors smaller than a unit one are described, it is to be understood that a scale factor may be greater than one. For example, it may be desirable to spin the instrument at a greater rate than a corresponding spin of the handle.

The controller 46 adds the incremental values _M1-_M5 to the initial joint angles Mj1-Mj5 in adder element 64 to provide values Mr1-Mrs. The controller 46 then computes desired slave vector calculations in computation block 66 in accordance with the following equations.

$$Rdx = Mr3 \cdot \sin(Mr2) \cdot \cos(Mr1) + Px$$

$$Rdy = Mr3 \cdot \sin(Mr2) \cdot \sin(Mr1) + Py$$

$$Rdz = Mr3 \cdot \cos(Mr2) + Pz$$

$$Sdr = Mr4$$

$$Sdg = Mr5$$

where;
Rdx, y, z=the new desired position of the end effector of the instrument.
Sdr=the angular rotation of the instrument about the instrument longitudinal axis.
Sdg=the amount of movement of the instrument fingers.
Px,y,z=the position of the pivot point P.

The controller 46 then computes the movement of the robotic arm 26 in computational block 68 in accordance with the following equations.

$$Jsd1 = Rdz$$

$$Jsd3 = \pi - \cos^{-1}\left[\frac{Rdx^2 + Rdy^2 - L1^2}{2L1 \cdot L2}\right]$$

$$Jsd2 = \tan^{-1}(Rdy/Rdx) + \Delta \text{ for } Jsd3 \leq 0$$

$$Jsd2 = \tan^{-1}(Rdy/Rdx) - \Delta \text{ for } Jsd3 \leq 0$$

$$\Delta = \cos^{-1}\left[\frac{Rdx^2 + Rdy^2 + L1^2 - L2^2}{2 \cdot L1\sqrt{Rdx^2 + Rdy^2}}\right]$$

$$Jds6 = Mr4$$

$$Jsd7 = Mr5$$

where;
Jsd1=the movement of the linear motor.
Jsd2=the movement of the first rotary motor.
Jsd3=the movement of the second rotary motor.
Jsd6=the movement of the rotational motor.
Jsd7=the movement of the gripper.
L1=the length of the linkage arm between the first rotary motor and the second rotary motor.
L2=the length of the linkage arm between the second rotary motor and the passive joints.

The controller provides output signals to the motors to move the arm and instrument in the desired location in block 70. This process is repeated for each movement of the handle.

The master handle will have a different spatial position relative to the surgical instrument if the surgeon releases, or toggles, the input button and moves the handle. When the input button 58 is initially depressed, the controller 46 computes initial joint angles Mj1-Mj5 in computational block 72 with the following equations.

$$Mj1 = \tan^{-1}(ty/tx)$$

$$Mj2 = \tan - 1(d/tz)$$

$$Mj3 = D$$

$$Mj4 = Js6$$

$$Mj5 = Js7$$

$$d = \sqrt{tx^2 + ty^2}$$

$$tx = \frac{Rsx - Px}{D} \quad ty = \frac{Rsy - Py}{D} \quad tz = \frac{Rsz - Pz}{D}$$

-continued $$D = \sqrt{(Rsx - Px)^2 + (Rsy - Py)^2 + (Psz - Pz)^2}$$

The forward kinematic values are computed in block 74 with the following equations.

$$Rsx = L1 \cdot \cos(Js2) + L2 \cdot \cos(Js2 + Js3)$$

$$Rsy = L1 \cdot \sin(Js2) + L2 \cdot \sin(Js2 + Js3)$$

$$Rsz = J1$$

Figure 5:
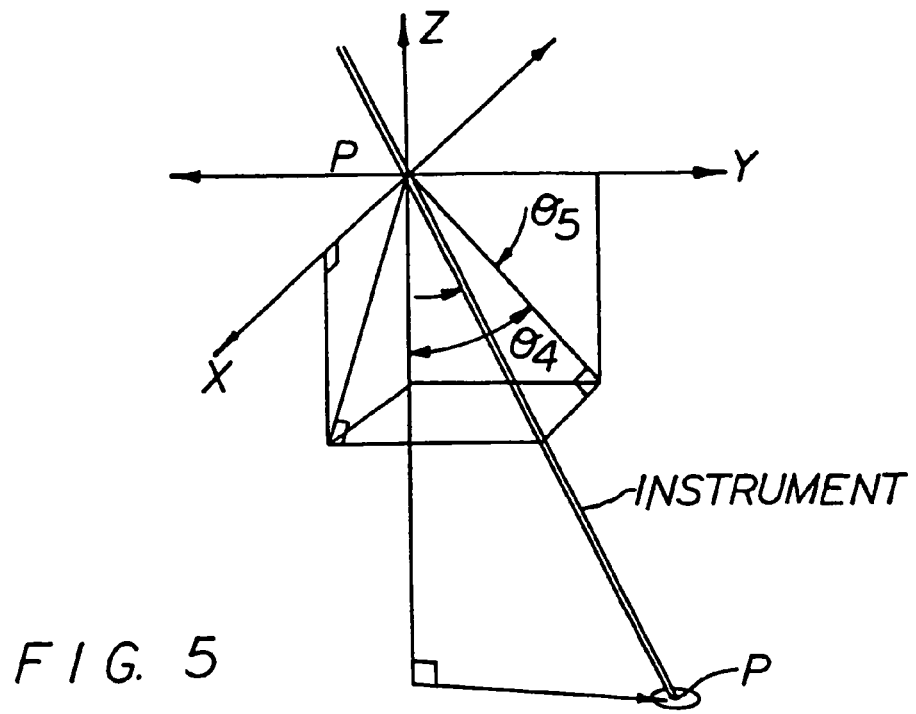
FIG. 5 is a schematic showing the instrument in a coordinate frame.

The joint angles Mj are provided to adder 64. The pivot points Px, Py and Pz are computed in computational block 76 as follows. The pivot point is calculated by initially determining the original position of the intersection of the end effector and the instrument PO, and the unit vector Uo which has the same orientation as the instrument. The position P(x, y, z) values can be derived from various position sensors of the robotic arm. Referring to FIG. 5 the instrument is within a first coordinate frame (x, y, z) which has the angles θ4 and θ5. The unit vector Uo is computed by the transformation matrix:

$$U_O = \begin{bmatrix} \cos\Theta_5 & 0 & -\sin\Theta_5 \\ -\sin\Theta_4\sin\Theta_5 & \cos\Theta_4 & -\sin\Theta_4\cos\Theta_5 \\ \cos\Theta_4\sin\Theta_5 & \sin\Theta_4 & \cos\Theta_4 \end{bmatrix} \begin{bmatrix} 0 \\ 0 \\ -1 \end{bmatrix}$$

After each movement of the end effector an angular movement of the instrument D Q is computed by taking the arcsin of the cross-product of the first and second unit vectors Uo and U1 of the instrument in accordance with the following line equations Lo and L1.

$$\Delta\theta = \arcsin(|T|)$$

$$T = Uo \times U1$$

where;

T=a vector which is a cross-product of unit vectors Uo and U1.

Figure 6:
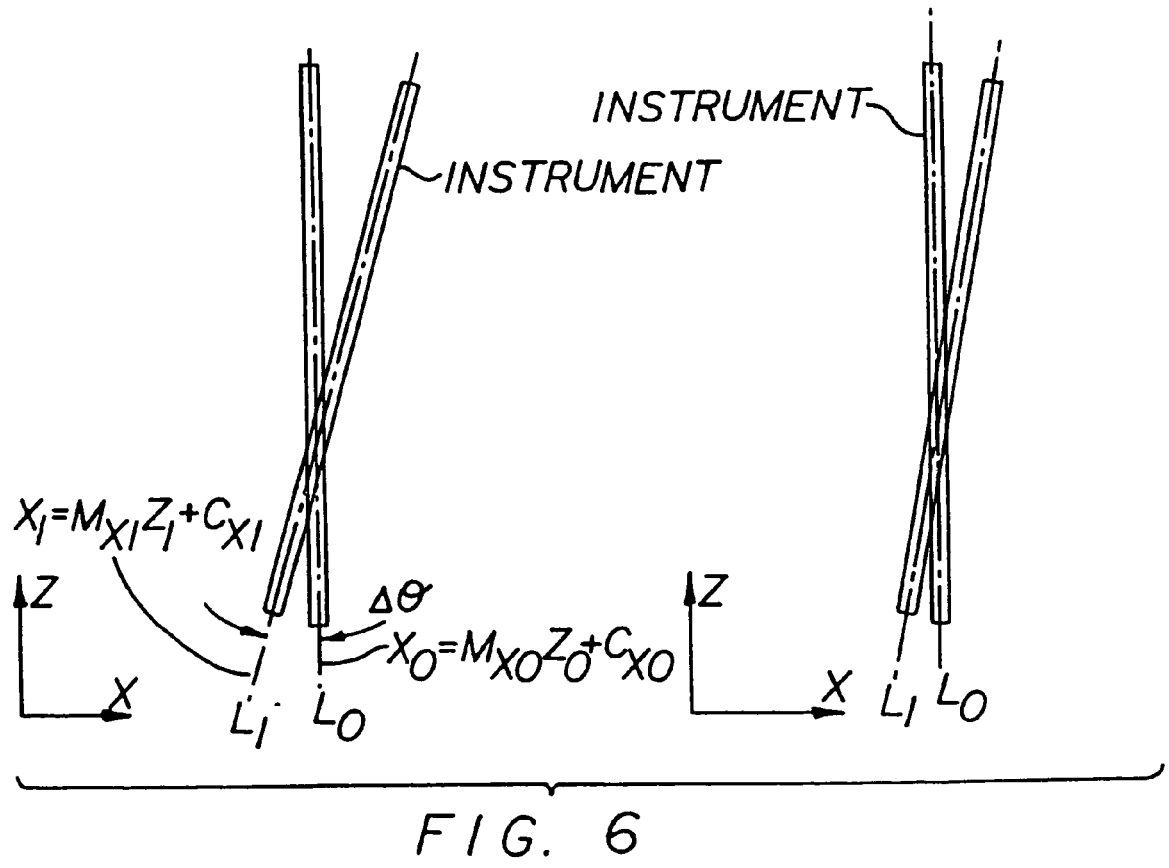
FIG. 6 is a schematic of the instrument moving about a pivot point.

The unit vector of the new instrument position U1 is again determined using the position sensors and the transformation matrix described above. If the angle θ9 is greater than a threshold value, then a new pivot point is calculated and Uo is set to U1. As shown in FIG. 6, the first and second instrument orientations can be defined by the line equations Lo and L1:

Lo:

$$xo = M_x0 \cdot Zo + Cxo$$

$$yo = M_yo \cdot Zo + Cyo$$

L1:

$$x1 = Mx1 \cdot Z1 + Cx1$$

$$y1 = My1 \cdot Z1 + Cy1$$

where;

Zo=a Z coordinate along the line Lo relative to the z axis of the first coordinate system.

Z1=a Z coordinate along the line L1 relative to the z axis of the first coordinate system.

Mxo=a slope of the line Lo as a function of Zo.

Myo=a slope of the line Lo as a function of Zo.

Mx1=a slope of the line L1 as a function of Z1.

My1=a slope of the line L1 as a function of Z1.

Cxo=a constant which represents the intersection of the line Lo and the x axis of the first coordinate system.

Cyo=a constant which represents the intersection of the line Lo and the y axis of the first coordinate system.

Cx1=a constant which represents the intersection of the L1 and the x axis of the first coordinate system.

Cy1=a constant which represents the intersection of the line L1 and the y axis of the first coordinate system.

The slopes are computed using the following algorithms:

$$Mxo = Uxo/Uzo$$

$$Myo = Uyo/Uzo$$

$$Mx1 = Ux1/Uz1$$

$$My1 = Uy1/Uz1$$

$$Cx0 = Pox - MX1 \cdot POZ$$

$$Cy0 = Poy - My1 \cdot Poz$$

$$Cx1 = P1x - Mx1 \cdot P1z$$

$$Cy1 = P1y - My1 \cdot P1z$$

where;

Uo (x, y and z)=the unit vectors of the instrument in the first position within the first coordinate system.

U1 (x, y and z)=the unit vectors of the instrument in the second position within the first coordinate system.

Po (x, y and z)=the coordinates of the intersection of the end effector and the instrument in the first position within the first coordinate system.

P1 (x, y and z)=the coordinates of the intersection of the end effector and the instrument in the second position within the first coordinate system.

To find an approximate pivot point location, the pivot points of the instrument in the first orientation Lo (pivot point Ro) and in the second orientation L1 (pivot point R1) are determined, and the distance halfway between the two points Ro and R1 is computed and stored as the pivot point Rave of the instrument. The pivot point Rave is determined by using the cross-product vector T.

To find the points Ro and R1 the following equalities are set to define a line with the same orientation as the vector T that passes through both Lo and L1.

$$tx = Tx/Tz$$

$$ty = Ty/Tz$$

where;

tx=the slope of a line defined by vector T relative to the Z-x plane of the first coordinate system.

ty=the slope of a line defined by vector T relative to the Z-y plane of the first coordinate system.

Tx=the x component of the vector T.

Ty=the y component of the vector T.

Tz=the z component of the vector T.

Picking two points to determine the slopes Tx, Ty and Tz (eg. Tx=x1−xo, Ty=y1−yo and Tz=z1−z0) and substituting the line equations Lo and L1, provides a solution for the point coordinates for Ro (xo, yo, zo) and R1 (x1, y1, z1) as follows.

$$zo = ((Mx1 - tx)z1 + Cx1 - Cxo)/(Mxo - tx)$$

$$z1 = ((Cy1 - Cyo)(Mxo - tx) - (Cx1 - Cxo)(Myo - ty))/((Myo - ty)(Mx1 - tx) - (My1 - ty)(Mxo - tx))$$

$$yo = Myo \cdot zo + Cyo$$

$$y1 = My1 \cdot z1 + Cy1$$

$$xo = Mxo \cdot zo + Cxo$$

$$x1 = Mx1 \cdot z1 + Cx1$$

The average distance between the pivot points Rc and R1 is computed with the following equation and stored as the pivot point of the instrument.

$$R_{ave} = ((x1+xo)/2, (y1+yo)/2, (z1+zo)/2$$

The pivot point can be continually updated with the above described algorithm routine. Any movement of the pivot point can be compared to a threshold value and a warning signal can be issued or the robotic system can become disengaged if the pivot point moves beyond a set limit. The comparison with a set limit may be useful in determining whether the patient is being moved, or the instrument is being manipulated outside of the patient, situations which may result in injury to the patient or the occupants of the operating room.

While substantial real time movement of the robotic arms is provided, it may be appreciated that pre-planned movements may be incorporated into the present system 10. This is, most advantageous with regard to movement of the endoscope. Any type of movement may be stored in am associated memory of the controller so that a surgeon may define his own favorite movements and then actuate such movement by pressing a button or via voice control. Because the movement is taught in the present application as well as those patents incorporated herein by reference, no further disclosure of this concept is required.

To provide feedback to the surgeon, the system 10 may include a voice feedback unit. As such, it the robotic arms suffer any malfunction, the voice feedback may supply a message that such error has occurred. Additionally, messages regarding instrument location, time-in-use, as well as a host of other data may be supplied to the surgeon through the voice feedback unit. If such a condition occurs that requires a message, the system has a set of messages stored in an associated memory, such message may be encoded and saved in the memory. A speech synthesis unit 89, as depicted in FIG. 1 can then vocalize the message to the surgeon. In this fashion, a surgeon can maintain sight of the operative environment as opposed to looking for messages displayed on a video screen or the like. Speech synthesis is well known, although its inclusion in a master-slave robotic system for minimally invasive surgery is heretofore unknown and present novel and unobvious advantages.

To provide feedback to the surgeon the fingers of the instruments may have pressure sensors that sense the reacting force provided by the object being grasped by the end effector. Referring to FIG. 4, the controller 46 receives the pressure sensor signals Fs and generates corresponding signals Cm in block 78 that are provided to an actuator located within the handle. The actuator provides a corresponding pressure on the handle which is transmitted to the surgeon's hand. The pressure feedback allows the surgeon to sense the pressure being applied by the instrument. As an alternate embodiment, the handle may be coupled to the end effector fingers by a mechanical cable that directly transfers the grasping force of the fingers to the hands of the surgeon.

Figure 7:
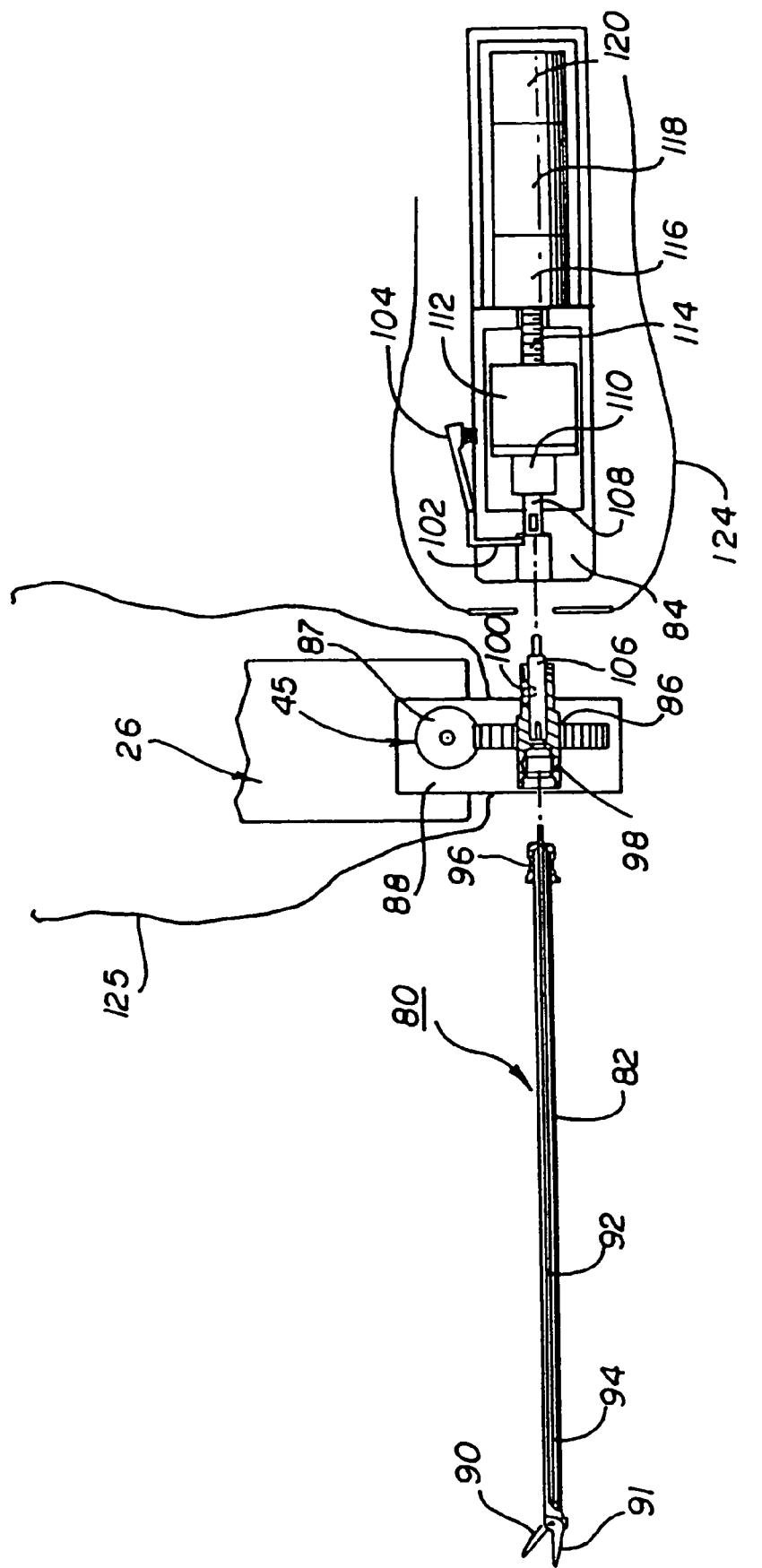
FIG. 7 is an exploded view of an end effector in accordance with the system of the present invention.

FIG. 7 shows a preferred embodiment of an end effector 80 that may be used in the present invention. The end effector 80 includes a surgical instrument 82, such as those disclosed hereinabove 22, 24, that is coupled to a front loading tool driver 84. The end effector 80 is mounted to one of the robotic arm assemblies 26 by coupling mechanism 45. The coupling mechanism 45 includes a collar 85 that removably attaches to a holder 86. The holder 86 includes a worm gear 87 that is driven by a motor in the robotic arm assembly 26 to rotate the collar 85 and in turn rotate the instrument 82 about its longitudinal axis. The holder 86 includes a shaft 88 that seats into a slot-in the robotic arm assembly 26. The shaft 88 may be turned by the motor in the arm assembly, which then rotates the worm gear 87 thus rotating the collar 86 and the instrument 82. A tightening tool 89 may be employed to tighten and loosen the collar about the instrument 82. Such a tool operates like a chuck key, to tighten and loosen the collar 86.

The surgical instrument 82 has a first finger 90 that is pivotally connected to a second finger 91. The fingers 90, 91 can be manipulated to hold objects such as tissue or a suturing needle. The inner surface of the fingers may have a texture to increase the friction and grasping ability of the instrument 82. The first finger 90 is coupled to a rod 92 that extends through a center channel 94 of the instrument 82. The instrument 82 may have an outer sleeve 96 which cooperates with a spring biased ball quick disconnect fastener 98. The quick disconnect 98 allows instruments other than the finger grasper to be coupled to front loading tool driver 84. For example, the instrument 82 may be decoupled from the quick disconnect 98 and replaced by a cutting tool, a suturing tool, a stapling tool adapted for use in this system, such as the stapling apparatus disclosed in U.S. Pat. Nos. 5,499,990 or 5,389,103 assigned to Karlsruhe, a cutting blade, or other surgical tools used in minimally invasive surgery. The quick disconnect 98 allows the surgical instruments to be interchanged without having to re-sterilize the front loading tool driver 84 each time an instrument is plugged into the tool driver 84. The operation of the front loading tool driver 84 shall be discussed in further detail hereinbelow.

The quick disconnect 98 has a slot 100 that receives a pin 102 of the front loading tool driver 84. The pin 102 locks the quick disconnect 98 to the front loading tool driver 100. The pin 102 can be released by depressing a spring biased lever 104. The quick disconnect 98 has a piston 106 that is attached to the tool rod 92 and in abutment with an output piston 108 of a load cell 110 located within the front loading tool driver 84.

The load cell 110 is mounted to a lead screw nut 112. The lead screw nut 112 is coupled to a lead screw 114 that extends from a gear box 116. The gear box 116 is driven by a reversible motor 118 that is coupled to an encoder 120. The entire end effector 80 is rotated by the motor driven worm gear 87.

In operation, the motor 118 of the front loading tool driver 84 receives input commands from the controller 46 via electrical wiring, or a transmitter/receiver system and activates, accordingly. The motor 118 rotates the lead screw 114 which moves the lead screw nut 112 and load cell 110 in a linear manner. Movement of the load cell 110 drives the coupler piston 106 and tool rod 92, which rotate the first finger 88. The load cell 110 senses the counteractive force being applied to the fingers and provides a corresponding feedback signal to the controller 46.

Figure 26:
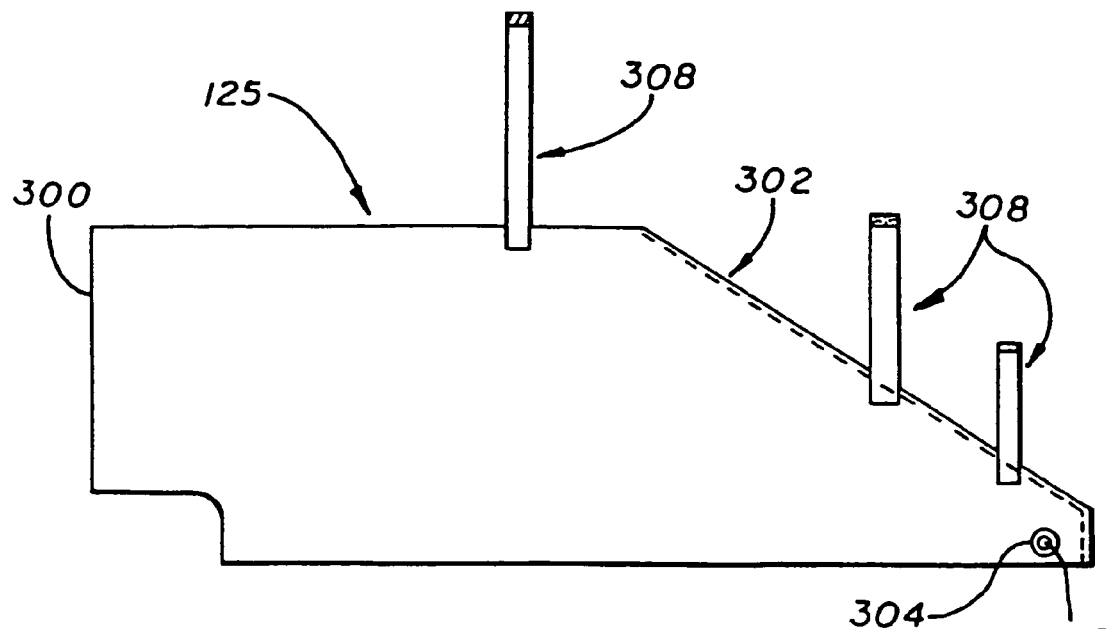
FIG. 26 is a plan view of a drape for use with the robotic arm in accordance with the present invention.

The front loading tool driver 84 may be covered with a sterile drape 124 so that the tool driver 84 does not have to be sterilized after each surgical procedure. Additionally, the robotic arm assembly 26 is preferably covered with a sterile drape 125 so that it does not have to be sterilized either. The drapes 124, 125 serve substantially as a means for enclosing the front loading tool driver 84 and robotic arm assembly 26. The drape 125 used to enclose the robotic arm assembly 26 is depicted in further detail in FIG. 26. The drape 125 has a substantially open end 300 wherein the robotic arm assembly 26 may be emplaced into the drape 125. The drape 125 additionally includes a substantially tapered enclosed end 302 that effectively separates the arm assembly 26 from the operating room environment. A washer 304 having a small aperture 306 formed therethrough allows an instrument to be coupled to the arm assembly 26 via the coupling mechanism 45. The washer 304 reinforces the drape 125 to ensure that the drape 125 does not tear as the arm assembly 26 moves about. Essentially, the instrument cannot be enclosed in the drape 125 because it is to be inserted into the patient 12. The drape 125 also includes a plurality of tape 308 having adhesive 310 disposed thereon. At least one piece of tape 308 is opposedly arranged the other pieces of tape 308 to effectuate the closing of the drape 125 about the arm assembly 26.

Figure 8:
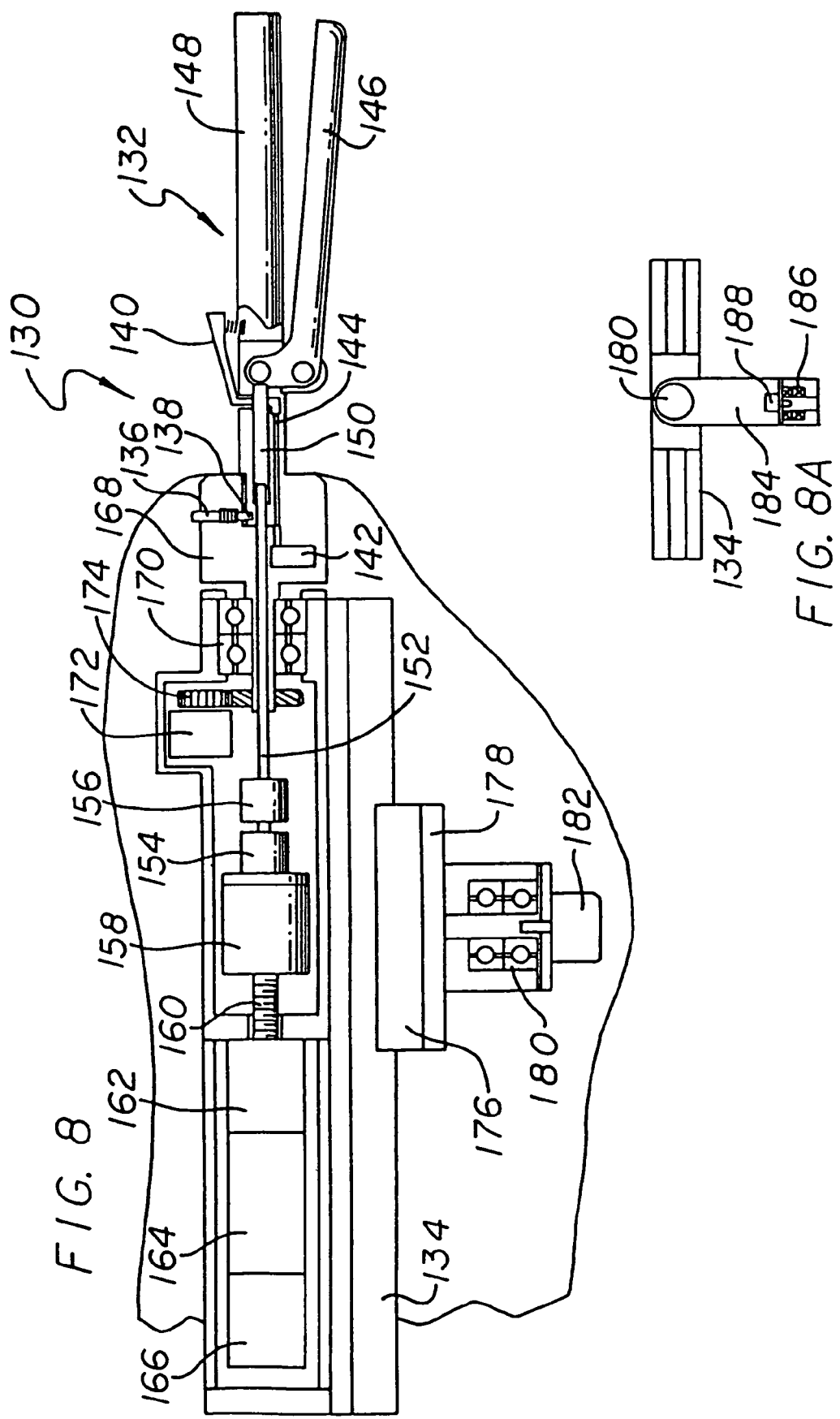
FIG. 8 is a view of a master handle of the system in accordance with the present invention.
Figure 9:
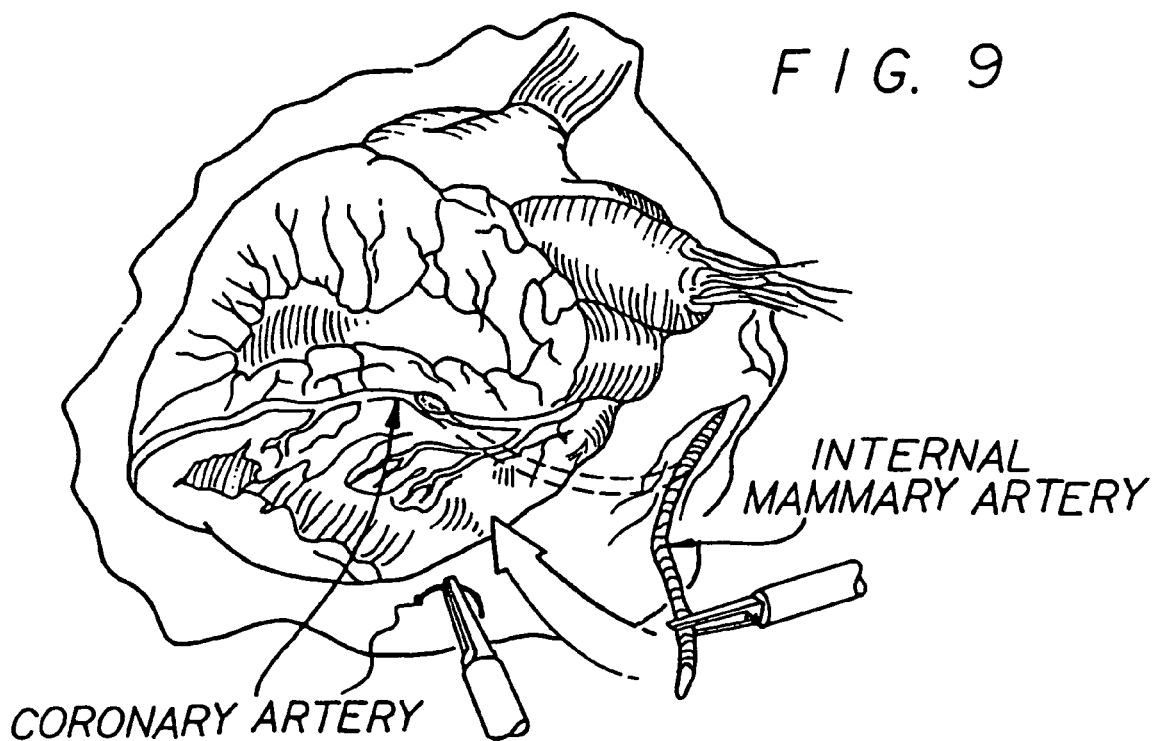
FIGS. 9-10A-I are illustrations showing an internal mammary artery being grafted to a coronary artery.

FIGS. 8 and 8a show a preferred embodiment of a master handle assembly 130. The master handle assembly 130 includes a master handle 132 that is coupled to an arm 134. The master handle 132 may be coupled to the arm 134 by a pin 136 that is inserted into a corresponding slot 138 in the handle 132. The handle 132 has a control button 140 that can be depressed by the surgeon. The control button 140 is coupled to a switch 142 by a shaft 144. The control button 140 corresponds to the input button 58 shown in FIG. 4, and activates the movement of the end effector.

The master handle 132 has a first gripper 146 that is pivotally connected to a second stationary gripper 148. Rotation of the first gripper 146 creates a corresponding linear movement of a handle shaft 150. The handle shaft 150 moves a gripper shaft 152 that is coupled a load cell 154 by a bearing 156. The load cell 154 senses the amount of pressure being applied thereto and provides an input signal to the controller 46. The controller 46 then provides an output signal to move the fingers of the end effector.

The load cell 154 is mounted to a lead screw nut 158 that is coupled to a lead screw 160. The lead screw 160 extends from a reduction box 162 that is coupled to a motor 164 which has an encoder 166. The controller 46 of the system receives the feedback signal of the load cell 110 in the end effector and provides a corresponding command signal to the motor to move the lead screw 160 and apply a pressure on the gripper so that the surgeon receives feedback relating to the force being applied by the end effector. In this manner the surgeon has a "feel" for operating the end effector.

The handle is attached to a swivel housing 168 that rotates about bearing 170. The swivel housing 168 is coupled to a position sensor 172 by a gear assembly 174. The position sensor 172 may be a potentiometer which provides feedback signals to the controller 46 that correspond to the relative position of the handle. Additionally, an optical encoder may be employed for this purpose. Alternatively, both a potentiometer and an optical encoder may be used to provide redundancy in the system. The swivel movement is translated to a corresponding spin of the end effector by the controller and robotic arm assembly. This same type of assembly is employed in the stand 900.

The arm 134 may be coupled to a linear bearing 176 and corresponding position sensor 178 which allow and sense linear movement of the handle. The linear movement of the handle is translated into a corresponding linear movement of the end effector by the controller and robotic arm assembly. The arm can pivot about bearings 180, and be sensed by position sensor 182 located in a stand 184. The stand 184 can rotate about bearing 186 which has a corresponding position sensor 188. The arm rotation is translated into corresponding pivot movement of the end effector by the controller and robotic arm assembly.

A human hand will have a natural tremor typically resonating between 6-12 hertz. To eliminate tracking movement of the surgical instruments with the hand tremor, the system may have a filter that filters out any movement of the handles that occurs within the tremor frequency bandwidth. Referring to FIG. 4, the filter 184 may filter analog signals provided by the potentiometers in a frequency range between 6-12 hertz. Alternatively, an optical encoder and digital filter may be used for this purpose.

As shown in FIGS. 9 and 10A-J, the system is preferably used to perform a cardiac procedure such as a coronary artery bypass graft (CABG). The procedure is performed by initially cutting three incisions in the patient and inserting the surgical instruments 22 and 24, and the endoscope 26 through the incisions. One of the surgical instruments 22 holds a suturing needle and accompanying thread when inserted into the chest cavity of the patient. If the artery is to be grafted with a secondary vessel, such as a saphenous vein, the other surgical instrument 24 may hold the vein while the end effector of the instrument is inserted into the patient.

The internal mammary artery (IMA) may be severed and moved by one of the instruments to a graft location of the coronary artery. The coronary artery is severed to create an opening in the artery wall of a size that corresponds to the diameter of the IMA. The incision(s) may be performed by a cutting tool that is coupled to one of the end effectors and remotely manipulated through a master handle. The arteries are clamped to prevent a blood flow from the severed mammary and coronary arteries. The surgeon manipulates the handle to move the IMA adjacent to the opening of the coronary artery. Although grafting of the IMA is shown and described, it is to be understood that another vessel such as a severed saphaneous vein may be grafted to bypass a blockage in the coronary artery.

Figure 10A:
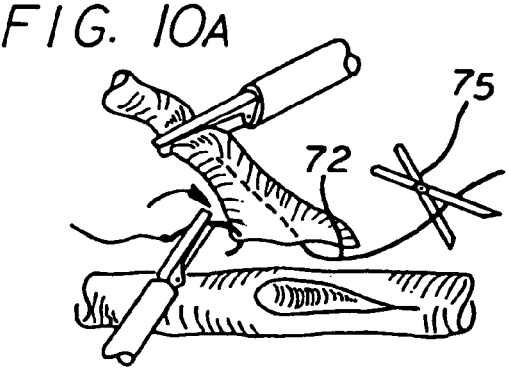
Figure 10B:
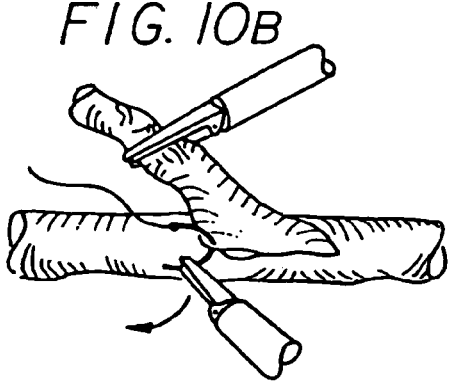
Figure 10C:
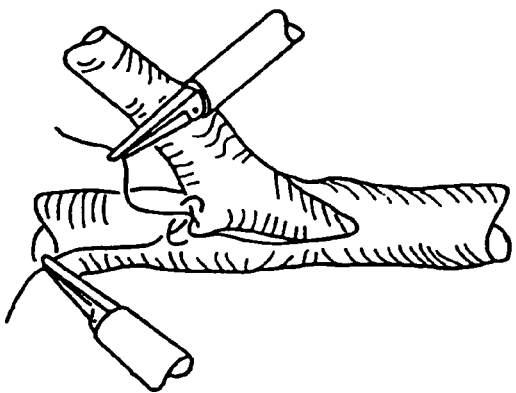
Figure 10D:
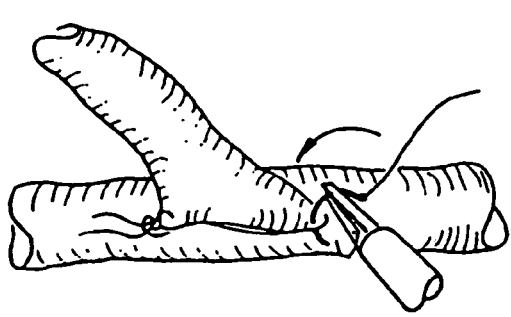
Figure 10E:
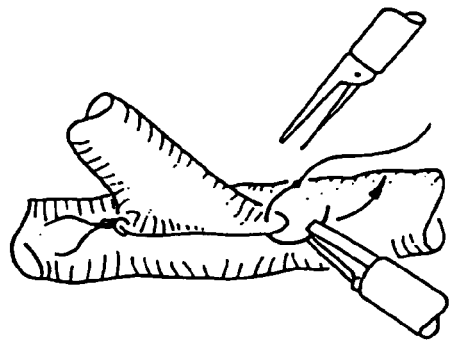
Figure 10F:
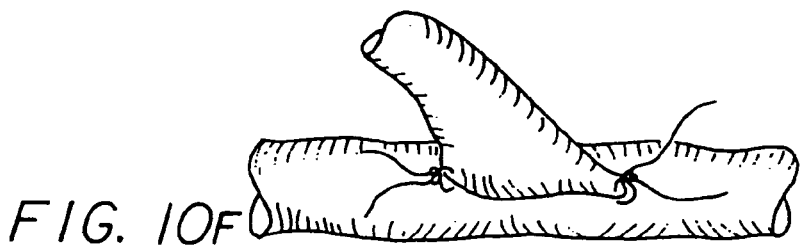
Figure 10G:
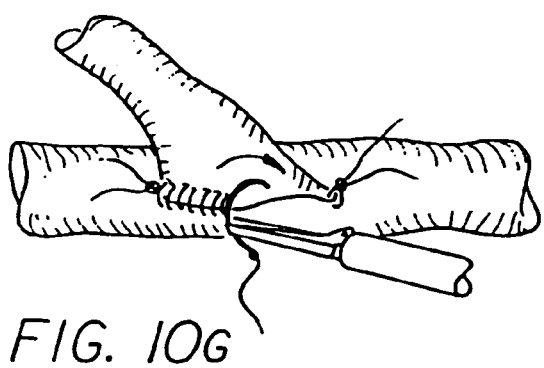
Figure 10H:
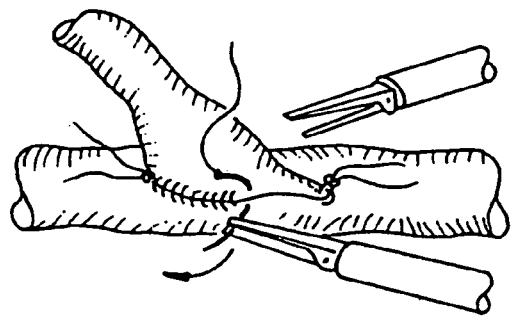
Figure 10I:
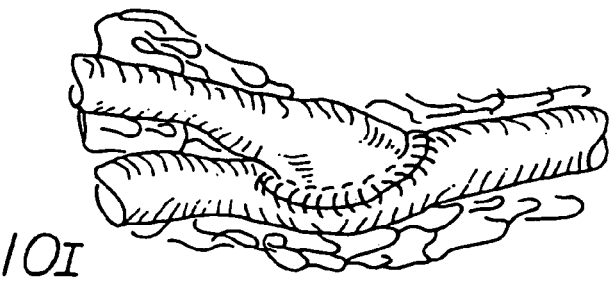
Figure 15:
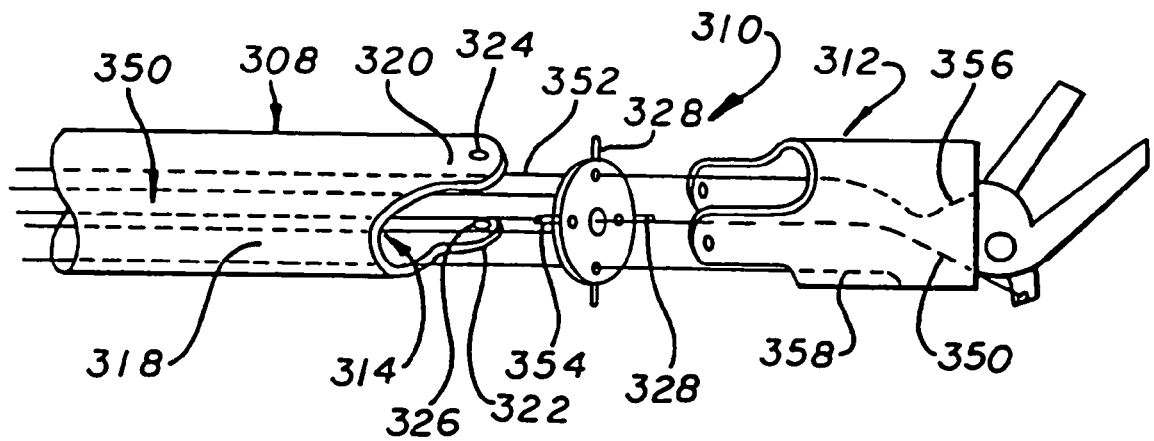
FIG. 15 is an exploded view of the articulable portion of the articulable instrument in accordance with the present invention.
Figure 16:
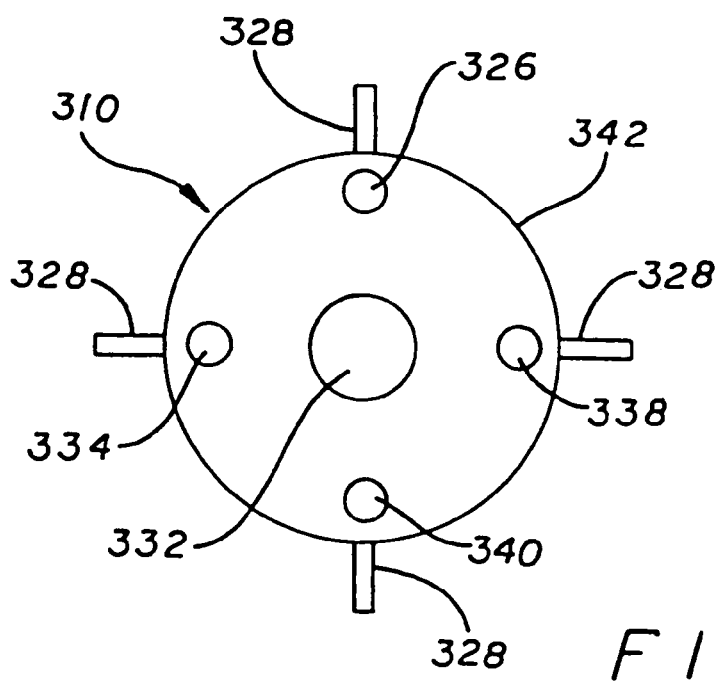
FIG. 16 is a plan view of a pivot linkage in accordance with the articulate portion of the articulable surgical instrument of the present invention.
Figure 17:
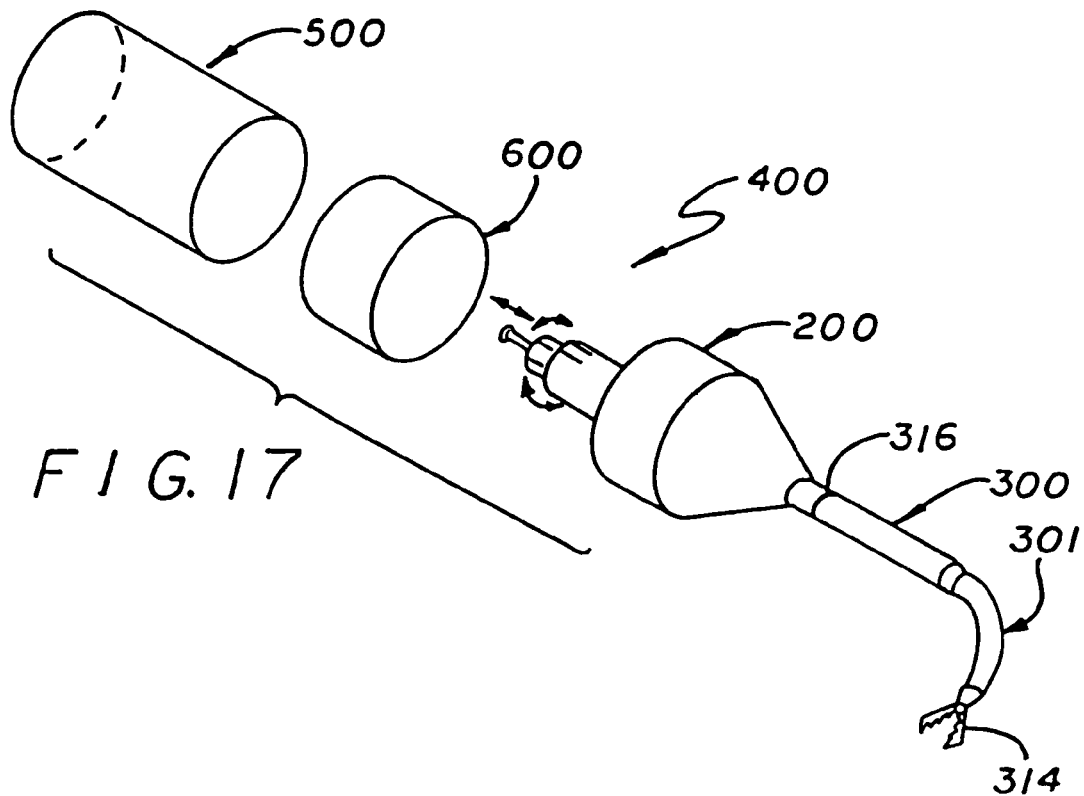
FIG. 17 is a perspective view of an articulating tool driving assembly in accordance with the present invention.

Referring to FIGS. 10A-J, the surgeon moves the handle to manipulate the instrument into driving the needle through the IMA and the coronary artery. The surgeon then moves the surgical instrument to grab and pull the needle through the coronary and graft artery as shown in FIG. 10B. As shown in FIG. 10C, the surgical instruments are then manipulated to tie a suture at the heel of the graft artery. The needle can then be removed from the chest cavity. As shown in FIGS. 10D-F, a new needle and thread can be inserted into the chest cavity to suture the toe of the graft artery to the coronary artery. As shown in FIG. 10H-J, new needles can be inserted and the surgeon manipulates the handles to create running sutures from the heel to the toe, and from the toe to the heel. The scaled motion of the surgical instrument allows the surgeon to accurately move the sutures about the chest cavity. Although a specific graft sequence has been shown and described, it is to be understood that the arteries can be grafted with other techniques. In general the system of the present invention may be used to perform any minimally invasive anastomostic procedure.

Additionally, it may be advantageous to utilize a fourth robotic arm to hold a stabilizer 75. The stabilizer may be a tube or wire or some other medical device that may be emplaced within an artery, vein or similar structure to stabilize such structure. Using the switch 51 to interengage the fourth robotic arm, with a handle 50 or 52 a surgeon may position the stabilizer 75 into the vessel. This eases the task of placing a stitch through the vessel as the stabilizer 75 maintains the position of the vessel. Once the stabilizer 75 has been placed, the surgeon then flips the switch or like mechanism to activate the robotic arm that had been disconnected to allow for movement of the fourth robotic arm. The stabilizer 75 should be substantially rigid and hold its shape. Additionally, the stabilizer should be formed form a material that is steralizable. Such material are well known in the medical arts. However, this application and configuration is heretofore unknown.

As disclosed hereinabove, the system may include a front loading tool driver 84 which receives control signals from the controller 46 in response to movement of a master handle 50 or 52 and drives the tool disposed at the end of a surgical instrument. Alternatively, a back loading tool driver 200 may be incorporated into the system 10 of the present invention, as depicted in FIGS. 11 and 11a. The back loading tool driver 200 cooperates with a back loadable surgical instrument 202. The incorporation of such a back loading tool driver 200 and instrument 202 expedites tool changing during procedures, as tools may be withdrawn from the tool driver 200 and replaced with other tools in a very simple fashion.

The back loading tool driver 200 is attached to a robotic arm assembly 26 via a collar and holder as disclosed hereinabove. The back loading tool driver includes a sheath 204 having a proximal end 206 and a distal end 208. The sheath 204 may be formed of plastic or some other well-known material that is used in the construction of surgical instruments. The sheath 204 is essentially a hollow tube that fits through the collar 85 and is tightened in place by the tightening tool that is described in more detail hereinabove.

The back loadable surgical instrument 202 has a tool end 210 and a connecting end 212. A surgical tool 214, such as a grasper or some other tool that may be driven by a push/pull rod or, cable system, or a surgical tool that does not require such a rod or cable, such as a coagulator, or harmonic scalpel is disposed at the tool end 210 of the instrument 202.

A housing 216 is disposed at the connecting end 212 of the instrument 202. The housing has a lever 218 disposed interiorly the housing 216. The lever 218 has a pivot point 220 that is established by utilizing a pin passing through an associated aperture 222 in the lever. The pin may be attached to the interior wall 224 of the housing. A push/pull cable or rod 226, that extends the length of the instrument 202 is attached to the lever 218, such that movement of the lever 218 about the pivot point; 220 results in a linear movement of the cable or rod 226. Essentially the cable or rod 226 servers as a means 227 for actuating the tool 214 at the tool end 210 of the instrument 202. The cable or rod 226 maybe attached to the lever via a connection pin as well. The lever 218 has a C-shape, wherein the ends of the lever 218 protrude through two apertures 228, 230 in the housing 216. The apertures 228, 230 are preferably surrounded by O-rings 232 the purpose of which shall be described in more detail hereinbelow.

The tool end 210 of the back loadable surgical instrument 202 is emplaced in the hollow tube of the back loading tool driver 200. The tool 202 may be pushed through the tool driver until the tool end 210 extends beyond the sheath 204. The O-rings 232 seat in associated apertures 234, 236 in a housing 238 of the tool driver 200. The housing additionally has-an aperture 240 centrally formed therethrough, the aperture being coaxial with the interior of the hollow tube. In this fashion, the surgical instrument 202 may be inserted into and through the tool driver 200. Each of the O-rings 232 snugly seats in its associated aperture in the housing 238 of the tool driver 200.

The housing 238 additionally includes a motor assembly 242 which is depicted in FIG. 11a. The motor assembly 242 is attached to the housing 238 and is held firmly in place therein. The motor assembly generally includes a motor 244 attached to a reducer 246. The motor drives a leaf 248 attached at the end thereof. The leaf 248 engages the ends of the lever 218 such that rotational movement of the motor results in the movement of the lever 218 about the pivot point 220. This in turn results in the lateral movement of the means 227 for actuating the tool 214 at the tool end 210 of the instrument 202. The motor moves in response to movements at a control handle. Additionally, force sensors 248, 250 may be attached at the ends of the leaf 248. As such, a force feedback system may be incorporated to sense the amount of force necessary to actuate the tool 214 at the tool end 210 of the instrument 202. Alternatively, the motor 244 may have a force feedback device 252 attached thereto, which can be used in a similar fashion.

One advantage of utilizing the back loading tool driver 200 is that the sheath 204 always remains in the patient 12. As such, the tools do not have to be realigned, nor does the robotic arm assembly 26 when replacing or exchanging tools. The sheath 204 retains its position relative to the patient 12 whether or not a toll is placed therethrough.

Figure 25:
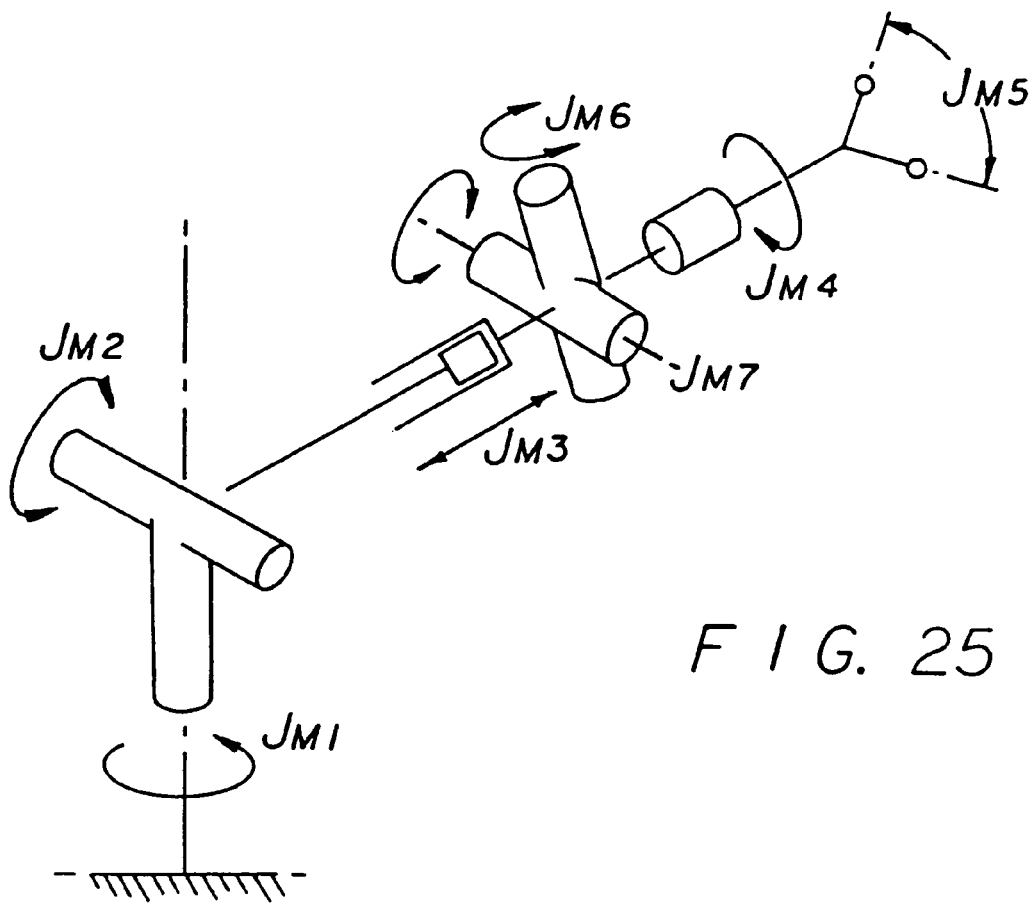
FIG. 25 is an schematic of a master of a system in accordance with the present invention that includes the articulating tool driving assembly.

The system 10 of the present invention may additionally be supplied with one or two additional degrees of freedom at the tip of an instrument. For the purposes of example, two additional degrees of freedom will be disclosed; however it is to be appreciated that only one degree of freedom may be included as well. To provide the additional degrees of freedom, and as depicted in FIGS. 13-16, an articulable surgical instrument 300 may be incorporated into the present. The instrument 300 may be coupled to the arm assembly 26 via a collar and holder as disclosed hereinabove. In order to articulate the tip of the articulable instrument 300 an articulating tool driver 500 must be employed. The articulating tool driver 500 shall be described in more detail hereinbelow. The master must have an additional two degrees of freedom added thereto to proved the controls for the articulation at the tip of the instrument 300. FIG. 25 depicts an alternative master schematic that includes the two additional degrees of freedom. As disclosed hereinbelow, the two additional degrees of freedom are mapped to the articulable portion of the instrument 300. The two additional axes at the master are referred to as Jm6 and Jm7.

By incorporating the articulable instrument 300 and the articulating tool driver 500 and the additional degrees of freedom at the master, difficult maneuvers may be carried out in an easier fashion.

With reference to FIGS. 13-16, the articulable instrument 300 generally includes an elongated rod 302, a sheath 309, and a tool 306. The tool can be a grasper, a cutting blade, a retractor, a stitching device, or some other well-known tool used in minimally invasive surgical procedures. FIGS. 27-30 show various tools that may be emplaced at the distal end of the articulable surgical instrument 300.

The instrument 300 includes an articulable portion 301 having a proximal portion 308, a pivot linkage 310 and a distal portion 212 each of which will be discussed in more detail hereinbelow. Additionally, the instrument 300 includes means 311 for articulating the articulable portion 301 of the instrument 300 with respect to the elongated rod 302. The inclusion of the articulable portion 301 provides two additional degrees of freedom at the instrument tip. It must also be appreciated that although the articulable portion 301 is described as including a proximal portion, a pivot linkage and a distal portion, there may be provided a plurality of intermediate portions each mounted to each other via a corresponding pivot linkage.

Disposed between and mounted to each of the respective proximal portion and distal portion and any intervening intermediate portions are pivot linkages 310. The pivot linkage 310 interrogates with the proximal and distal portions of the articulable portion to provide articulation at the instrument tip. Essentially, the cooperation of the proximal portion, pivot linkage and distal portion serves as a universal joint.

The elongated rod 302 is preferably hollow and formed of stainless steel or plastic or some other well-know material that is steralizable. Because the rod 302 is hollow, it encompasses and defines an interior 314. The elongated rod 302 additionally has a proximal end 316 and a distal end 318. The distal end 318 of the elongated rod 302 should not be confused with the distal portion 312 of the articulable portion 301 of the instrument 300.

The proximal portion 308 of the articulable portion 301 may be integrally formed with the elongated rod 302 or it may be attached thereto vie welding, glue or some other means well-known to the skilled artisan. It is preferable that the proximal portion 308 be integrally formed with the elongated rod 302 to ensure sufficient stability and durability of the instrument 300. The proximal portion 308 of the articulable portion 301 comprises two fingers 320, 322 each of which have an aperture 324, 326 formed therethrough.

A pivot linkage 310 is mounted to the proximal portion 308 via a plurality of pins 328 that each pass through an associated aperture in an adjoining finger. The pivot linkage 310 is a generally flat disk 330 having a central aperture 332 passing therethrough and four apertures 334, 336, 338, 340 evenly spaced at the periphery of the disk 330. Additionally pins 328 are attached to and extend from the edge 342. The pins 328 seat in the apertures of the associated fingers to provide the articulability of the instrument 300. Five leads 350, 352, 354, 356, 358 extend interiorly the hollow shaft. On lead 350 extends down the center and passes through the center aperture 332 in the pivot linkage 310. Two 352, 354 of the five leads extend down the hollow interior of the instrument and are attached to the pivot linkage such that linear tension on one of the leads results in rotational movement of the pivot portion 301. These two leads 352, 354 attach to the pivot linkage at two of the apertures formed therethrough. Additionally, they attach at those apertures that are adjacent to the pins that pass through the fingers of the proximal portion 308 of the articulable portion 301 of the instrument 300. The other two leads 356, 358 pass through the two other apertures in the pivot linkage and attach at the distal end of the articulable portion 301.

Movement of these two leads results in movement of the articulable portion 301 that is orthogonal to the movement when the two other leads 352, 354 are moved.

To articulate the instrument as a part of the present system, and as depicted in FIGS. 17-24, there is provided an articulating mechanism 400. The articulating mechanism 400 generally comprises the articulating tool driver 500, a sterile coupler 600, a translator 700 and the articulable tool 300.

Figure 18:
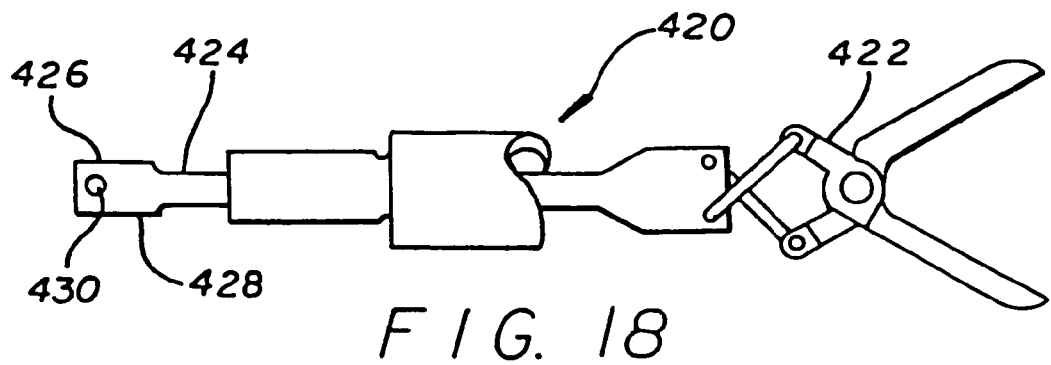
FIG. 18 is a view of a removable tool-tip in accordance with an articulable instrument of the present invention.
Figure 19:
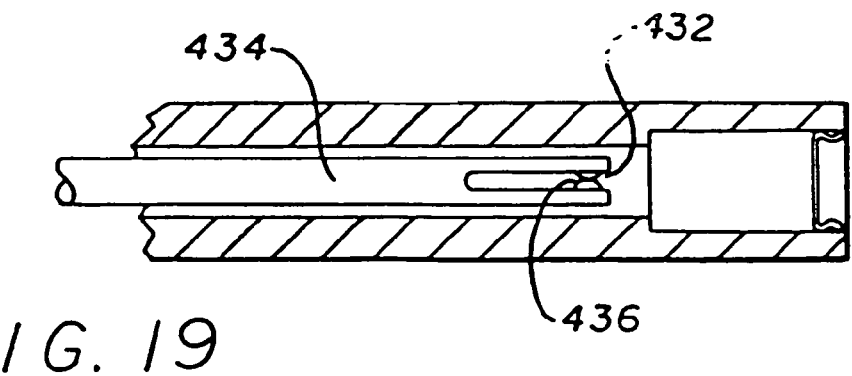
FIG. 19 is a tool-tip receptacle in accordance with the present invention.
Figure 23:
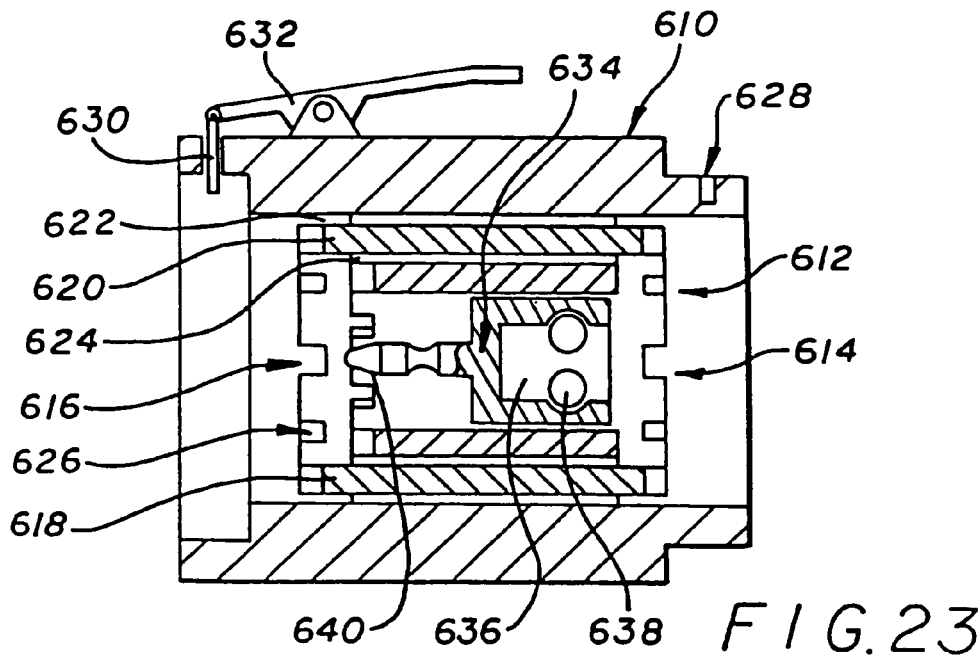
FIG. 23 is a cross-sectional view of the sterile section of the articulating tool driving assembly in accordance with the system of the present invention.
Figure 24:
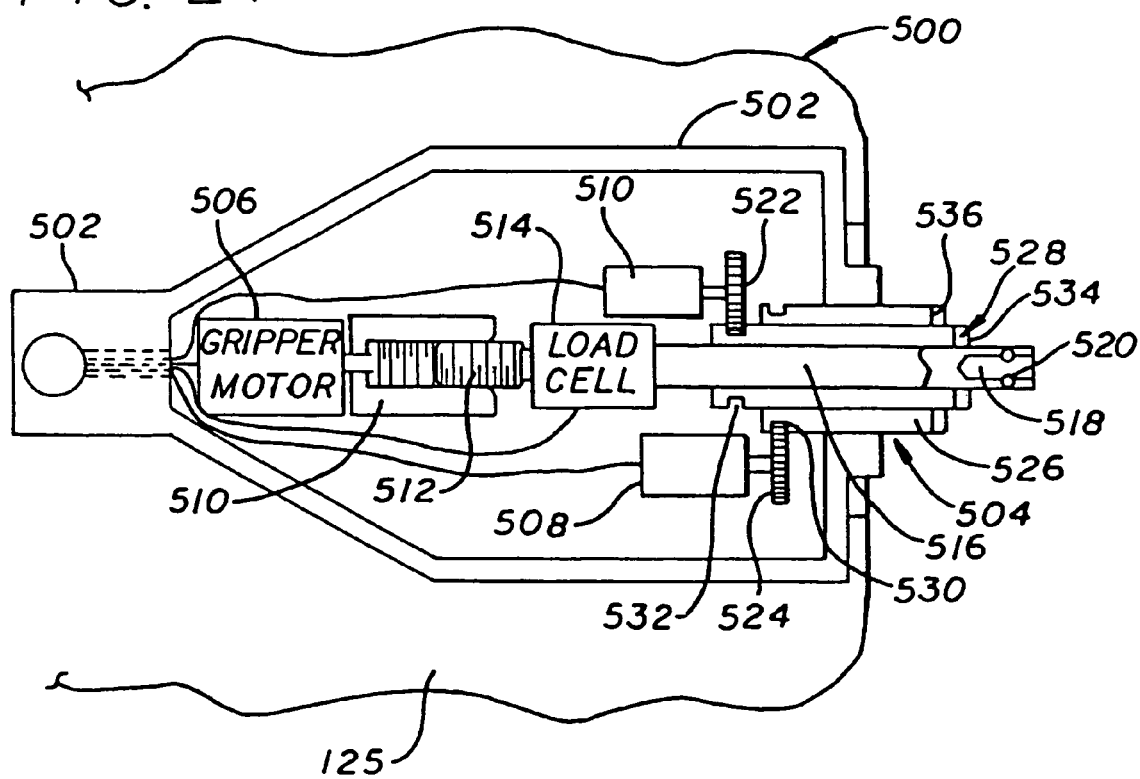
FIG. 24 is a cross sectional view of the tool driver of the articulating tool driving assembly in accordance with the system of the present invention.

The translator is attached to the proximal end 316 of the instrument 300. The instrument 300 may additionally have a removable tool 420 as shown in FIGS. 18-19. The removable tool 420 may be any tool, such as a cutter 422 that is attached to an elongated rod or cable 424. At the end of the rod 246 there is disposed a flat section 428 with an aperture 430 formed therethrough. The flat section 428 seats into a channel 432 disposed at the end of a second cable or rod 434 that travels down the elongated shaft of the instrument 300. The second cable 434 has a channel 432 formed in the end thereof such that the flat section 428 seats in the channel 432. At least one spring biased detent 436 seats in the aperture 430 disposed through the flat section 428. This connects the tool 420 to the rest of the instrument 300. As such, tools may be exchanged at the tip of the instrument without having to remove the instrument from the system 10 every time a new tool is required.

The tool 300 is attached to the translator 700 and essentially is integrally formed therewith. The articulating mechanism 400 is attached to the robotic arm assembly 26 via the collar 85 as is disclosed hereinabove. The collar 85 fits about the shaft 302 of the instrument 300.

The translator 700 has a proximal end 702 and a distal end 704. The distal end 704 of the translator 700 has a cross sectional shape that is substantially similar to the cross sectional shape of the elongated rod 302 of the instrument 300. Additionally, the translator 700 has a hollow interior 706. The center rod 350 extends through the hollow interior 706 of the translator 700 and emerges at the proximal end 702 thereof. Two of the leads 352, 354 terminate interiorly the translator at two shoulders 708, 710 that are attached to a first hollow tube 712 through which the center lead 350 extends. The first hollow tube 712 may be formed of some strong durable material such as stainless steel, steel, hard plastic or the like.

The first hollow tube 712 is mounted to a bearing 714 such that it may be rotated. Rotation of the first hollow tube 712 results in the linear motion of the leads 352, 254 and the articulation of the articulable portion 301 of the instrument 300 in one plane of motion.

A second hollow tube 716 has a pair of shoulders 718, 719 extending therefrom. Two leads 356, 358 attach to one each of the shoulders 718, 719. The hollow tube 716 is disposed within a bearing assembly 720 such that it may be rotated. Again, rotation of the second hollow tube 716 results in linear movement of the leads 356, 358 which articulates the articulable portion 301 of the instrument 300 in a plane orthogonal the plane of motion established through the rotation of the first hollow tube. It is to be appreciated that the second hollow tube 714 radially surrounds the first hollow tube 712. The translator 700 additionally includes a quick disconnect 722 comprising a pin 724 disposed at the end of a spring biased lever 726 which provides removable attachment of the translator 700 to the sterile coupler 600. Both of the hollow tubes 712 and 716 may have notches 750 formed therein at their ends. The notches serve as a means 752 for interconnecting each of the tubes to the sterile coupler 600 which will be discussed in further detail hereinbelow.

The translator 700 is removably attached to the sterile coupler 600 via the quick disconnect 722. Because the articulable tool driver 500 is not easily sterilized, it is advantageous to include a sterile coupler 600 so that instruments may be exchanged without having to sterilize the articulable tool driver 500. Additionally, the coupler 600 provides a means by which the translator 700 may be attached to the tool driver 500 while the tool driver is enclosed in a drape 125 such as that depicted in FIG. 26. The translator 600 has a housing 610. Preferably the housing and the components of the coupler 600 are formed of some easily steralizable material such as stainless steel, plastics or other well-known sterilizable materials. The housing 610 has a substantially hollow interior 612 and open ends 614 and 616. Two hollow tubes 618 and 620 are rotatively disposed within the housing 610. To effectuate the rotation of each of the tubes 618 and 620, bearings 622 and 624 are disposed about each of the tubes. Each of the tubes has notches -626 formed in the ends thereof so effectuate the attachment of the translator 700 to the coupler 600 at one end. And to effectuate the attachment of the coupler 600 to the articulable tool driver 500 at the other end thereof.

The pin 724 on the translator may seat in a notch 628 to attach the translator 700 to the coupler 600. Additionally, the coupler 600 may include a pin 630 attached to a spring biased pivot 632 to effectuate attachment of the coupler to the driver 500. The coupler 600 additionally includes a center section 634 that slidably receives the end 351 of the center cable or rod 350. The end 351 may include a tip with a circumferential groove 353 disposed thereabout. The tip seats in a recess 636 formed in the center section 634 and is removably locked in place by at least one spring biased detent 638. A tip 640, which is substantially similar to the tip containing the circumferential groove 353 is disposed adjacent the recess 636 and serves to attach the cable center cable 350 to the articulable tool driver 500, which will be discussed in further detail hereinbelow.

The center section 634 is intended to laterally slide within the innermost tube 618. To effectuate such a sliding motion, a linear bearing may be disposed about the center section interiorly of the innermost tube. Alternatively, the center section 634 may be formed of a bearing material that provides smooth sliding within the innermost tube 618.

The coupler 600 is removably attached to the articulable tool driver 500. It is intended that the articulable tool driver be enclosed by a drape 125. The articulable tool driver 500 includes a substantially hollow housing 502 having a closed first end 504 and a substantially open second end 504. Securely disposed interiorly the housing 502 is a gripper motor 506, and a pair of wrist motors 508 and 510. Each of the motors are in electrical connection with the controller 46. Alternatively, the motors may receive signals from the controller via a transmitter/receiver system where such systems are well known. It is the application of such a transmitter/receiver system to the present invention that is new. The gripper motor 506 is attached to a load nut 510 that surrounds a load screw 512. The motor 506 receives the control signals and turns in response thereto. The load nut 510 turns which laterally moves the load screw 512. The load screw 512 is attached to a load cell which may be employed to measure the force required to laterally move the cable 350 which is attached vie the coupler- 600 to the gripper motor 506. This may be used in a force feedback system that may be incorporated in the system 10 of the present invention. A rod 516 having a channel 518 formed at the end thereof is attached to the load cell 514. As such, the rod 516 moves in a linear fashion. The tip 640 of the coupler 600 seats in the channel 518 and is removably held in place by at least one spring biased detent or some other similar attachment mechanism 520. Therefore, if a surgeon at a master handle actuates the grippers, the gripper motor 506 turns, thus laterally moving the rod 516, and in turn the center cable 350 which opens and closes the grippers at the tool accordingly. Of course, the action at the tool will depend upon the type of tool disposed thereat. For example, if a stapling tool is disposed at the end of the surgical instrument 300 then a stapling action would take place.

If a master handle 50 or 52 is turned about axes J6 or J7 then one of the two wrist motors 510, 508 corresponding to the required motion turns. Each of the motors 508, 510 are attached to a corresponding gear 522, 524. Each of the gears 522, 524 engage a corresponding slotted section 530, 532 of an associated hollow tube 526, 528 to turn the associated tube radially about its longitudinal axis. Each of the tubes 526, 528 include notched ends 534, 536 to engage the notched ends of corresponding hollow tubes of the coupler 600. It is to be appreciated that each of the hollow tubes 526, 528, 618 and 620 are all coaxial. Additionally, bearings may be emplaced intermediate each of the tubes 526 and 528 to provide easy independent rotatability of the individual tubes.

When the tubes 526, 528 are rotated, they rotate the tubes in the coupler which rotates the tubes in the translator. This results in the articulation at the tip of the surgical instrument 300. More particularly, this results in the articulation of the articulable portion of the surgical instrument 300. Additionally, whether the front loading tool driver, the back loading tool driver, or the articulable tool driver are employed, surgical instruments may be easily exchanged.

As such, a cutting blade 800 may be exchanged for a grasper, and a grasper may be exchanged for a stapler 810. Essentially, such a system simplifies the performance of minimally invasive surgical procedures where the procedures include the step of changing one tool for another. And because the system allows articulation at the tip of certain instruments, the articulation mechanism may be used to articulate such stapling, or cutting instruments that incorporate the articulable portion as disclosed hereinabove.

Figure 27:
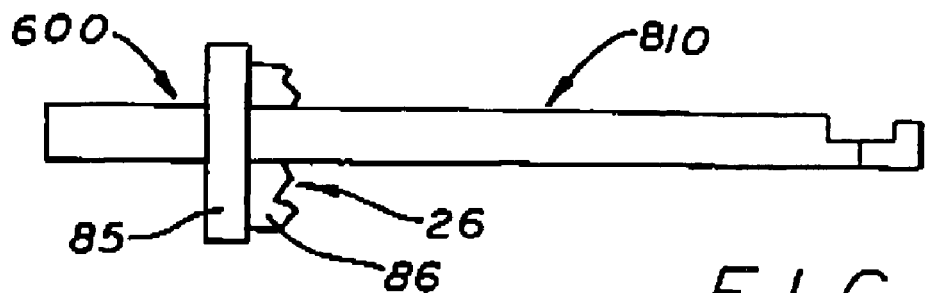
FIG. 27 is a plan view of a surgical instrument having a stapling tool disposed at the end thereof and wherein the surgical instrument is attached to the robotic arm in accordance with the present invention.

Additionally, the instrument may not be an articulable instrument, but the articulating mechanism can be used to control other functions, such as stapling. FIG. 27 depicts a stapling instrument 810 attached to the robotic arm assembly via the collar 85 and holder 86. The lead that is generally use for the grasping tool, may be used to effectuate the stapling mechanism. Endoscopic staplers are generally well known in the art, however, it is heretofore to known to use a stapler that is attached to a robotic arm as is disclosed herein.

Figure 28:
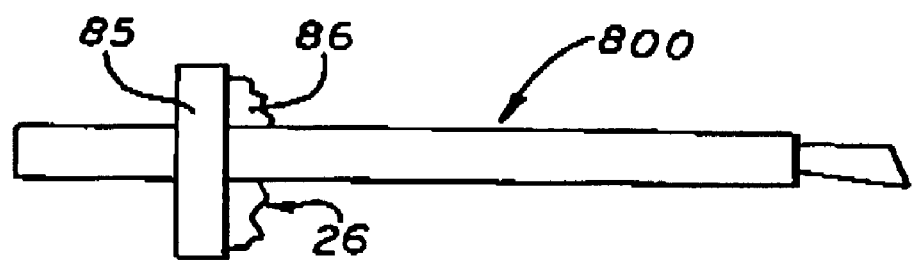
FIG. 28 is a plan view of a surgical instrument having a cutting blade disposed at the end thereof wherein the instrument is attached to the robotic arm in accordance with the present invention.
Figure 29:
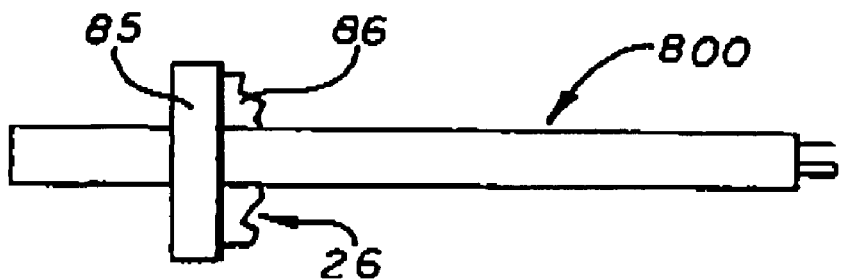
FIG. 29 is a plan view of a surgical instrument having a coagulating/cutting device disposed at the end thereof, the instrument attached to a robotic arm in accordance with the present invention.
Figure 30:
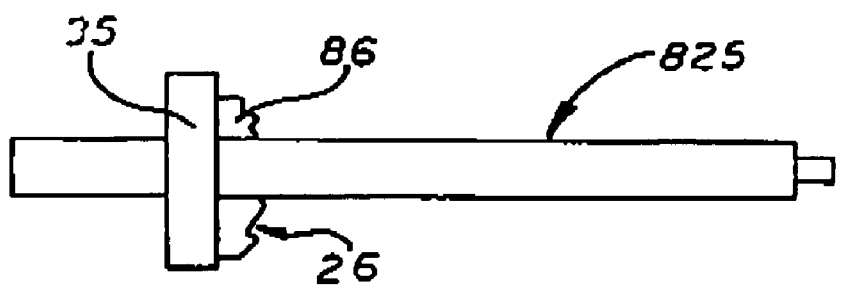
FIG. 30 is a plan view of a surgical instrument having a suturing tool disposed at the end thereof and wherein the surgical instrument is attached to the robotic arm in accordance with the present invention.

Additionally, a cutting blade, such as that depicted in FIG. 28 may be employed in the system of the present invention. The cutting blade 800 is attached to the robotic arm assembly 26 via the collar 85 and holder 86. The cutting blade does not require a lead such as that required by the grasper or the stapler; however, the cutting tool, may be articulated via the articulating mechanism that has been disclosed hereinabove.

A cauterizer or coagulator may additionally be attached to the robotic arm assembly 26 via the collar 85 and holder. Cauterizers and coagulators are well known and the cauterizing tool may be attached at the end of an articulable instrument as disclosed hereinabove. By using a variety of tools in predetermined sequences, various procedures may be carried out. It is generally preferable to be able to change instruments because many procedures require such.

As disclosed hereinabove, the handles 50 and 52 allow a surgeon to control the movement of the tools attached to the robotic arms. As such, the configuration of the handles 50 and 52 should provide great ease of use for a surgeon. FIGS. 34-39 depict various handle configurations. Additionally, the handles 50 and 52 may be selected by a surgeon from a plurality of handles 960 that are available for use by the surgeon.

A proximally open handle 962 has a proximal end 963 and a distal end 965. The handle 962 has first finger portion 964 and a second finger portion 966 pivotally attached at the distal end 965 of the handle 962. A joint 968 disposed intermediate the finger portion 964 and 966 provides linear motion of an elongated rod 970 which is used to actuate the tool tip of an instrument attached to the robotic arm. This handle may serve as one or both of the two handles 50 and 52 of the system.

A distally open handle 972 has a proximal end 973 and a distal end 975. The handle 972 has first finger portion 974 and a second finger portion 976 pivotally attached at the proximal end 973 of the handle 972. A joint 978 disposed intermediate the finger portion 964 and 966 provides linear motion of an elongated rod 980 which is used to actuate the tool tip of an instrument attached to the robotic arm. This handle may serve as one or both of the two handles 50 and 52 of the system.

Such handles 962 and 972 may be interchanged through the inclusion of an interchange mechanism 984. The interchange mechanism 984 includes a biased detent latch 986 that engages an aperture in the elongated rod 932 such that the handle may be attached or removed from the rod 932.

Other handle configurations are depicted in FIGS. 37-39. And more particularly, each of the handles 1000, 1100, and 1200 have a pair of fingerseats 1020. The major difference between each of the handles 1000, 1100, and 1200 is the orientation of the fingerseats to a pivot point on the handle. The fingerseats may be parallel, or perpendicular to the axis S of the pivot point of the handle. Each of these configurations may be included as an attachable handle. As such, a surgeon may exchange handles throughout a procedure depending upon the task to be accomplished. A surgeon may prefer one handle for a set of tasks and another handle for a different set of tasks. As such, the surgeon may exchange handles during the performance of a surgical procedure to enable such tasks.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical robotic system comprising:
   a robotic arm;
   a surgical instrument coupled to the robotic arm, wherein the surgical instrument comprises an end effector;
   an input device; and
   a controller coupled to the robotic arm and to the input device;
   wherein the controller, in response to receiving a signal that a surgeon has moved the input device in a first degree of freedom, outputs a command to move the end effector in a first corresponding degree of freedom, the movement of the end effector in the first corresponding degree of freedom being scaled by a first scaling factor to the movement of the input device in the first degree of freedom;
   wherein the controller, in response to receiving a signal that the surgeon has moved the input device in a second degree of freedom, outputs a command to move the end effector in a second corresponding degree of freedom, the movement of the end effector in the second corresponding degree of freedom being scaled by a second scaling factor to the movement of the input device in the second degree of freedom; and
   wherein the first and second scaling factors are different non-1 values.

2. The medical robotic system of claim 1, wherein the first scaling factor has a value more than 1 and the second scaling factor has a value less than 1.

3. The medical robotic system of claim 1, wherein the first and second scaling factors have non-zero values less than 1.

4. The medical robotic system of claim 1, wherein the first and second scaling factors have values more than 1.

5. The medical robotic system of claim 1, wherein the controller is configured to allow the surgeon to vary the first scaling factor in a range that includes a zero value.

6. The medical robotic system of claim 1, wherein the controller is configured to allow the surgeon to vary the first and second scaling factors.

7. The medical robotic system of claim 1, wherein movement of the end effector has been filtered to remove a hand tremor of the surgeon.

8. The medical robotic system of claim 1, wherein the controller is configured to store a preplanned movement of one of the surgical instruments and to allow the surgeon to actuate the preplanned movement.

9. The medical robotic system of claim 1:
   wherein the end effector is selected from a group consisting of a gripper, a stapling tool, a cutting device, a coagulating device, and a suturing tool; and
   wherein the medical robotic system further comprises:
   a second robotic arm;
   a second surgical instrument coupled to the second robotic arm, wherein the second surgical instrument comprises an endoscope;
   a third robotic arm;
   a third surgical instrument coupled to the third robotic arm, wherein the third robotic arm comprises a tissue stabilizer;
   a fourth robotic arm; and
   a fourth surgical instrument coupled to the fourth robotic arm.

10. The medical robotic system of claim 9, wherein the tissue stabilizer comprises a blood vessel stabilizer.

11. A medical robotic system comprising:
    a robotic arm;
    a surgical instrument coupled to the robotic arm, wherein the surgical instrument comprises an end effector;
    an input device; and
    a controller coupled to the robotic arm and to the input device;
    wherein the system is configured to allow the surgeon to activate the input device such that movement of the input device in a first direction moves the end effector in a corresponding direction;
    wherein the system is configured to allow the surgeon to deactivate the input device such that when the surgeon moves the input device in a direction opposite the first direction the end effector remains stationary;
    wherein the system is configured to allow the surgeon to reactivate the input device such that movement of the input device in the first direction further moves the end effector in the corresponding direction;
    wherein before deactivating the input device the end effector moves as a function of a first scaling factor applied to the movement of the input device in the first direction;
    wherein after reactivating the input device the end effector moves as a function of a second scaling factor applied to movement of the input device in the first direction; and
    wherein the first and second scaling factors are different non-1 values.

12. The medical robotic system of claim 11, wherein the activation, deactivation, and reactivation of the input device is controlled with a button.

13. The medical robotic system of claim 11, wherein the activation, deactivation, and reactivation of the input device is controlled with voice commands.

14. The medical robotic system of claim 11, wherein movement of the end effector is filtered to remove a hand tremor of the surgeon.

15. The medical robotic system of claim 11, wherein the controller is configured to store a preplanned movement of one of the surgical instruments and to allow the surgeon to actuate the preplanned movement.

16. The medical robotic system of claim 11:
wherein the end effector is selected from a group consisting of a gripper, a stapling tool, a cutting device, a coagulating device, and a suturing tool; and
wherein the medical robotic system further comprises:
a second robotic arm;
a second surgical instrument coupled to the second robotic arm, wherein the second surgical instrument comprises an endoscope;
a third robotic arm;
a third surgical instrument coupled to the third robotic arm, wherein the third robotic arm comprises a tissue stabilizer;
a fourth robotic arm; and
a fourth surgical instrument coupled the fourth robotic arm.

17. The medical robotic system of claim 16, wherein the tissue stabilizer comprises a blood vessel stabilizer.

* * * * *